(12) United States Patent
Inoue et al.

(10) Patent No.: US 12,208,148 B2
(45) Date of Patent: *Jan. 28, 2025

(54) DENTAL RESTORATIVE CURABLE COMPOSITION

(71) Applicant: KURARAY NORITAKE DENTAL INC., Kurashiki (JP)

(72) Inventors: Masashi Inoue, Niigata (JP); Seiya Ichikawa, Niigata (JP); Kenji Suzuki, Niigata (JP); Hayato Miyakawa, Niigata (JP); Tatsuya Kajikawa, Niigata (JP); Hirotaka Horiguchi, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 637 days.

This patent is subject to a terminal disclaimer.

(21) Appl. No.: 17/605,951

(22) PCT Filed: Apr. 23, 2020

(86) PCT No.: PCT/JP2020/017553
§ 371 (c)(1),
(2) Date: Oct. 22, 2021

(87) PCT Pub. No.: WO2020/218446
PCT Pub. Date: Oct. 29, 2020

(65) Prior Publication Data
US 2022/0218572 A1 Jul. 14, 2022

(30) Foreign Application Priority Data
Apr. 24, 2019 (JP) .................. 2019-082971
Dec. 24, 2019 (JP) .................. 2019-233578

(51) Int. Cl.
| | | |
|---|---|---|
| A61K 6/889 | (2020.01) | |
| A61K 6/62 | (2020.01) | |
| A61K 6/64 | (2020.01) | |
| A61K 6/71 | (2020.01) | |

(52) U.S. Cl.
CPC .............. *A61K 6/889* (2020.01); *A61K 6/62* (2020.01); *A61K 6/64* (2020.01); *A61K 6/71* (2020.01)

(58) Field of Classification Search
CPC .................................................. A61K 6/887
See application file for complete search history.

(56) References Cited

U.S. PATENT DOCUMENTS

| | | | |
|---|---|---|---|
| 5,744,511 A | | 4/1998 | Kazama et al. |
| 10,973,742 B2* | | 4/2021 | Sakamaki ............. B33Y 70/00 |
| 2005/0049326 A1 | | 3/2005 | Park et al. |
| 2011/0046260 A1 | | 2/2011 | Okubayashi et al. |
| 2013/0172441 A1 | | 7/2013 | Takahata et al. |
| 2015/0182315 A1 | | 7/2015 | Okada et al. |
| 2017/0224591 A1 | | 8/2017 | Vogel et al. |
| 2017/0333167 A1* | | 11/2017 | Hagiwara ............. A61C 13/087 |
| 2018/0282455 A1 | | 10/2018 | Sakamaki et al. |

FOREIGN PATENT DOCUMENTS

| | | |
|---|---|---|
| EP | 3 494 954 A1 | 6/2019 |
| EP | 3 590 489 A1 | 1/2020 |
| EP | 3 735 957 A1 | 11/2020 |
| GB | 1 451 262 | 9/1976 |
| JP | 51-6224 | 1/1976 |

(Continued)

OTHER PUBLICATIONS

International Search Report issued on Jul. 7, 2020 in PCT/JP2020/017553 filed on Apr. 23, 2020, 2 pages.

(Continued)

*Primary Examiner* — Michael F Pepitone
(74) *Attorney, Agent, or Firm* — Oblon, McClelland, Maier & Neustadt, L.L.P.

(57) ABSTRACT

A dental restorative curable compositions may have a high mechanical strength and excellent water resistance and polishability in the form of a cured product. A dental composite resin may include such compositions. A dental mill blank may include the cured product of such compositions. A dental restorative curable composition may include: a (meth)acrylic acid ester compound (A) having two or more (meth)acryloyloxy groups per molecule; a mono(meth)acrylic acid ester compound (B); an inorganic filler (C) having an average primary particle diameter of 0.01 to 5 μm; and a polymerization initiator (D). The mono(meth)acrylic acid ester compound may include at least one selected from the group consisting of a mono (meth)acrylic acid ester compound (B-1) of formula (I):

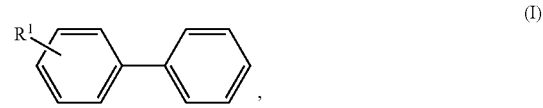

and a mono(meth)acrylic acid ester compound (B-2) of formula (II):

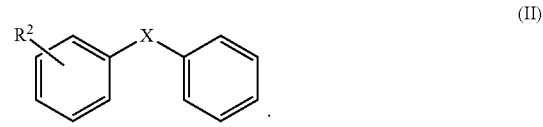

17 Claims, No Drawings

(56) References Cited

FOREIGN PATENT DOCUMENTS

| | | |
|---|---|---|
| JP | 1-113478 A | 5/1989 |
| JP | 9-3109 A | 1/1997 |
| JP | 10-245525 A | 9/1998 |
| JP | 2007-126417 A | 5/2007 |
| JP | 2014-185337 A | 10/2014 |
| JP | 2016-8211 A | 1/2016 |
| WO | WO 2012/042911 A1 | 4/2012 |
| WO | WO 2014/021343 A1 | 2/2014 |
| WO | WO 2017/061446 A1 | 4/2017 |
| WO | WO-2018025943 A1 * | 2/2018 ............. A61C 13/01 |
| WO | WO 2018/074605 A1 | 4/2018 |
| WO | WO 2018/230657 A1 | 12/2018 |

OTHER PUBLICATIONS

Extended European Search Report issued Apr. 26, 2023 (client received on May 12, 2023, in corresponding European Patent Application No. 20794665.8, 15 pages.
S. Syed et al., "Treatment of oily water using hydrophobic nano-silica", Chemical Engineering Journal, 167, 2011, pp. 99-103.
European Office Action issued Jul. 13, 2022 in European Patent Application No. 20794665.8, 5 pages.
Scientific Documentation Tetric EvoCeram®/Tetric EvoFlow®, Ivoclar Vivadent AG Clinical, Sep. 2006, 30 pages.

* cited by examiner

DENTAL RESTORATIVE CURABLE COMPOSITION

CROSS-REFERENCE TO RELATED APPLICATIONS

The present application is the national stage of international application PCT/JP2020/017553, filed on Apr. 23, 2020, and claims the benefit of the filing date of Japanese Appl. No. 2019-082971 and 2019-233578, respectively filed on Apr. 24 and Dec. 24, 2019.

TECHNICAL FIELD

The present invention relates to a dental restorative curable composition that is suitably used as a dental material, particularly a dental composite resin, that can serve as a substitute for part or the whole of a natural tooth in the field of dentistry, and to a dental mill blank comprising a cured product of the dental restorative curable composition.

BACKGROUND ART

Dental restorative curable compositions composed of a polymerizable monomer, a filler, and a polymerization initiator are called dental composite resins, and are dental materials most widely used today as materials for restoring lost parts and caries of teeth. Dental composite resins are required, in the form of a cured product obtained after polymerization and curing, to have a sufficient mechanical strength to serve as a substitute for natural teeth, water resistance that can withstand long-term intraoral restoration, and polishability for obtaining a gloss equivalent to that of natural teeth, and are required, in the form of a paste before polymerization and curing, to have handling properties suitable for filling cavities using a dental instrument or the like.

Meanwhile, dental mill blanks are materials used for fabricating dental prosthesis such as inlays and crowns by CAD/CAM systems in which design is performed by computers and machining is performed by milling machines, and the demand for the dental mill blanks has increased rapidly in recent years. As a dental mill blank, a suitably sized block of a shape such as a rectangular parallelepiped, a cylinder, or a disc is supplied and set on a milling machine, and milled into a restoration having a shape of crown, dentition, or the like. Various types of materials as materials for dental mill blanks have been proposed, including glass ceramics, zirconia, titanium, acrylic resins, and composite materials containing a polymer resin and an inorganic filler. Dental mill blanks are also required to have a sufficient mechanical strength to serve as a substitute for natural teeth, water resistance that can withstand long-term intraoral restoration, and polishability for obtaining a gloss equivalent to that of natural teeth.

CITATION LIST

Patent Literature

Patent Literature 1: JP 2007-126417 A
Patent Literature 2: JP 2016-8211 A
Patent Literature 3: WO 2014/021343

SUMMARY OF THE INVENTION

Technical Problem

To achieve excellent paste handling properties and a high curability, a technique has been proposed on a mixture of a (meth)acrylic acid ester compound having two or more (meth)acryloyloxy groups per molecule and an aromatic ring, in which a hydroxy-group-containing body and a no-hydroxy-group-containing body are combined with each other (Patent Literature 1). However, studies conducted by the present inventors revealed a problem that addition of fine particles for achieving polishability deteriorates paste handling properties and lowers mechanical strength and water resistance.

In addition, to achieve excellent paste handling properties, a high mechanical strength after curing, and polishability, a technique of combining a mono(meth)acrylamide compound and a (meth)acrylic acid ester compound has been proposed (Patent Literature 2). However, studies conducted by the present inventors revealed a problem in this technique that mechanical strength is low and water resistance is also low.

With respect to dental mill blanks, for example, to achieve mechanical strength and polishability, a method for producing a dental mill blank is described according to which an inorganic filler is press-molded to obtain a molded body and a polymerizable monomer is immersed in the molded body for thermal polymerization (Patent Literature 3). This producing method allows dense filling with nanoparticles, obtaining a dental mill blank that is excellent in mechanical strength and polishability. However, studies conducted by the present inventors revealed a problem that when a polymerizable monomer having a high mechanical strength after curing is used to exhibit a high mechanical strength, the polymerizable monomer has a high viscosity and does not penetrate into the molded body. Further, water resistance is not mentioned and needs to be improved.

The present invention was made to solve the above problems in the conventional arts, and aims to provide a dental restorative curable composition that has, in the form of a cured product, a high mechanical strength and excellent water resistance and polishability, a dental composite resin comprising the dental restorative curable composition, and a dental mill blank comprising the cured product of the dental restorative curable composition. The present invention also aims to provide a dental restorative curable composition that is excellent in paste handling properties and a dental composite resin comprising the dental restorative curable composition. The present invention further aims to provide a dental mill blank with a suppressed air bubble generation in the form of a cured product and an excellent appearance.

Solution to Problem

As a result of intensive studies to achieve the above aims, the present inventors found that, by comprising a (meth)acrylic acid ester compound having two or more (meth)acryloyloxy groups per molecule, a specific mono(meth)acrylic acid ester compound, an inorganic filler having an average primary particle diameter of 0.01 to 5 μm, and a polymerization initiator, a dental restorative curable composition can be surprisingly obtained that has high mechanical strength, water resistance, and polishability in the form of a cured product and is excellent in paste properties before curing. The present inventors conducted further studies based on the finding to complete the present invention.

Specifically, the present invention includes the following.

[1] A Dental restorative curable composition comprising:
a (meth)acrylic acid ester compound (A) having two or more (meth)acryloyloxy groups per molecule;
a mono(meth)acrylic acid ester compound (B);
an inorganic filler (C) having an average primary particle diameter of 0.01 to 5 μm; and a polymerization initiator (D), wherein
the mono(meth)acrylic acid ester compound (B) comprises at least one selected from the group consisting of a mono(meth)acrylic acid ester compound (B-1) represented by the following general formula (I) and a mono(meth) acrylic acid ester compound (B-2) represented by the following general formula (II),

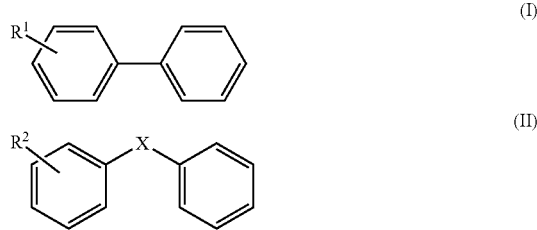

where $R^1$ and $R^2$ each independently represent a group represented by the following general formula (i) or a group represented by the following general formula (ii), and X is a divalent hydrocarbon group having 1 to 6 carbon atoms or an oxygen atom,

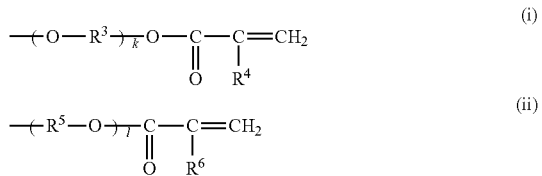

where $R^3$ and $R^5$ each independently represent a divalent hydrocarbon group having 1 to 10 carbon atoms, $R^4$ and $R^6$ each independently represent a hydrogen atom or a methyl group, and k and l are each independently an integer of 0 to 6.

[2] The dental restorative curable composition according to [1], wherein a content of the inorganic filler (C) is 50 to 95 mass % with respect to a total amount of the dental restorative curable composition.

[3] The dental restorative curable composition according to [1] or [2], wherein the mono(meth)acrylic acid ester compound (B) comprises the mono(meth)acrylic acid ester compound (B-2) represented by the general formula (II).

[4] The dental restorative curable composition according to [3], wherein X is an oxygen atom.

[5] The dental restorative curable composition according to any one of [1] to [4], wherein k and l are each 0 or 1.

[6] The dental restorative curable composition according to any one of [1] to [5], wherein the (meth)acrylic acid ester compound (A) comprises a compound having a ring structure.

[7] The dental restorative curable composition according to [6], wherein the compound having a ring structure is a compound (A-1) having an aromatic ring.

[8] The dental restorative curable composition according to [7], wherein the compound (A-1) having an aromatic ring is a compound having a bisphenol A skeleton.

[9] The dental restorative curable composition according to any one of [1] to [8], wherein the (meth)acrylic acid ester compound (A) comprises a compound having none of a hydroxy group, a carboxy group, a primary amino group, a secondary amino group, an amide group, a urea bond, and a urethane bond.

[10] The dental restorative curable composition according to any one of [1] to [9], wherein the dental restorative curable composition is essentially free of a compound having a heterocyclic ring that contains a nitrogen atom and having a polymerizable functional group.

[11] The dental restorative curable composition according to any one of [1] to [10], wherein the polymerization initiator (D) comprises a photopolymerization initiator.

[12] The dental restorative curable composition according to any one of [1] to [11], wherein the polymerization initiator (D) comprises a thermal polymerization initiator.

[13] The dental restorative curable composition according to any one of [1] to [12], further comprising a polymer.

[14] The dental restorative curable composition according to [13], wherein the polymer is a prepolymer having an unreacted polymerizable functional group.

[15] The dental restorative curable composition according to [14], wherein the number of unreacted polymerizable functional groups per molecule in the prepolymer is 5 or more and 1,000 or less.

[16] The dental restorative curable composition according to [14] or [15], wherein a weight-average molecular weight of the prepolymer is 1,000 or more and 1,000,000 or less.

[17] A dental composite resin comprising the dental restorative curable composition according to any one of [1] to [16].

[18] A dental mill blank comprising the dental restorative curable composition according to any one of [1] to [16].

Advantageous Effects of Invention

A dental restorative curable composition of the present invention has in the form of a cured product, a high mechanical strength and excellent water resistance and polishability. Also, the dental restorative curable composition of the present invention is excellent in paste handling properties. Further, the dental restorative curable composition of the present invention can suppress air bubble generation in the form of a cured product, and is excellent in appearance.

DESCRIPTION OF EMBODIMENTS

A dental restorative curable composition of the present invention comprises: a (meth)acrylic acid ester compound (A) having two or more (meth)acryloyloxy groups per molecule; a mono(meth)acrylic acid ester compound (B); an inorganic filler (C) having an average primary particle diameter of 0.01 to 5 μm; and a polymerization initiator (D). It is important that the mono(meth)acrylic acid ester compound (B) comprise at least one selected from the group consisting of a mono(meth)acrylic acid ester compound (B-1) represented by the above general formula (I) and a mono(meth)acrylic acid ester compound (B-2) represented by the above general formula (II).

Although the reason why the effects of the present invention can be obtained by the above structure is not necessarily clear, the present inventors assume as follows. It is known that fine particles are added to achieve polishability required for dental materials. However, a dental restorative curable composition obtained by mixing the fine particles and a polymerizable monomer has a problem of high viscosity and ease of undesired stickiness, that is, a problem that when filling a cavity with a dental instrument, the dental restorative curable composition adheres to the instrument to exhibit poor handling properties. On the other hand, although a polymerizable monomer having a low viscosity is sometimes used to improve handling properties, the cured product obtained tends to have a low mechanical strength. By using a mono(meth)acrylic acid ester compound (B) comprising at least one selected from the group consisting of a mono(meth)acrylic acid ester compound (B-1) represented by the above general formula (I) and a mono(meth)acrylic acid ester compound (B-2) represented by the above general formula (II), the viscosity can be suppressed low, the dental restorative curable composition obtained can have improved handling properties and exhibits a high mechanical strength in the formed of a cured product. The factor for improvement in mechanical strength is assumed as follows. A π-π interaction by an aromatic ring contained in the mono(meth)acrylic acid ester compound (B) strengthens an interaction between polymer chains after polymerization thereby to improve the mechanical strength of the cured product. In addition, by using the mono(meth)acrylic acid ester compound (B), the viscosity can be suppressed low and air bubble generation in the cured product can be suppressed.

The following describes the present invention in detail. In the present specification, the upper limits and lower limits of numeric ranges (for example, ranges of contents of components, ranges of values calculated from components, ranges of values of physical properties) can be combined appropriately. In the present specification, the numeric values represented by symbols in various formulae also can be combined as appropriate.

[(Meth)Acrylic Acid Ester Compound (A) Having Two or More (Meth)Acryloyloxy Groups Per Molecule]

A (meth)acrylic acid ester compound (A) having two or more (meth)acryloyloxy groups per molecule is used, in a dental restorative curable composition of the present invention, to impart water resistance and mechanical strength to a cured product of the dental restorative curable composition. The (meth)acrylic acid ester compound (A) having two or more (meth)acryloyloxy groups per molecule in the present invention (hereinafter, referred to also as "(meth) acrylic acid ester compound (A)") is not particularly limited, as long as the effects of the present invention are exhibited and a known (meth)acrylic acid ester compound for use in dental composite resins and the like is used. However, it is preferable to comprise a compound having a ring structure that is a rigid skeleton to improve the mechanical strength after curing. Examples of the compound having a ring structure include a compound (A-1) having an aromatic ring, a compound (A-2) having an alicyclic ring, and a compound (A-3) having a heterocyclic ring. A (meth)acrylic acid ester compound (A) (for example, a compound (A-1) having an aromatic ring, a compound (A-2) having an alicyclic ring, and a compound (A-3) having a heterocyclic ring) may be a monofunctional polymerizable compound having one or more polymerizable functional groups other than two or more (meth)acryloyloxy groups or may be a difunctional polymerizable compound having only two (meth)acryloyloxy groups per molecule, as long as the compound has two or more (meth)acryloyloxy groups per molecule. In the present invention, a (meth)acryloyloxy group and other polymerizable functional group are collectively referred to as "polymerizable functional group". Examples of the polymerizable functional group in the (meth)acrylic acid ester compound (A) include the similar one to that in a prepolymer described below, and preferred is a (meth) acryloyl group, and more preferred is a (meth)acryloyloxy group. Hereinafter, for example, a compound (A-3) having a heterocyclic ring is referred to also as "compound (A-3) having a heterocyclic ring and having a polymerizable functional group" and the like. One preferred embodiment is a dental restorative curable composition in which a polymerizable functional group in a (meth)acrylic acid ester compound (A) is only a (meth)acryloyloxy group. Another preferred embodiment is a dental restorative curable composition in which a polymerizable functional group in a compound (A-1) having an aromatic ring or a compound (A-2) having an alicyclic ring is only a (meth)acryloyloxy group.

Further, in view of further improving the mechanical strength after curing owing to a π-π interaction with a mono(meth)acrylic acid ester compound (B) described later, the (meth)acrylic acid ester compound (A) more preferably comprises a compound (A-1) having an aromatic ring, and even more preferably comprises a compound having a bisphenol A skeleton. In the present invention, the expression "(meth)acrylic" is used to include both methacrylic and acrylic. The same applies to the expression "(meth)acryloyl" and the like.

Examples of the (meth)acrylic acid ester compound (A) in the present invention are shown below.

Examples of an aromatic ring of the compound (A-1) having an aromatic ring include benzene, naphthalene, anthracene, biphenyl, benzophenone, phenyl ether, and bisphenol A, and bisphenol A is preferred in view of further improving the mechanical strength and the water resistance of the cured product when combined with a mono(meth) acrylic acid ester compound (B). Examples of the compound (A-1) having an aromatic ring include 2,2-bis[4-[3-acryloyloxy-2-hydroxypropoxy]phenyl]propane, 2,2-bis[4-(3-methacryloyloxy-2-hydroxypropoxy)phenyl]propane (commonly known as "Bis-GMA"), 2,2-bis[4-[2-(acryloyloxy)ethoxy]phenyl]propane, 2,2-bis[4-[2-(methacryloyloxy)ethoxy]phenyl]propane (commonly known as "Bis-MEPP"), 2,2-bis[4-(meth)acryloyloxypolyethoxyphenyl] propane (for example, the average addition number of moles of an ethoxy group is 2.6), 1,2-bis[3-(meth)acryloyloxy-2-hydroxypropoxyphenyl]ethane, and 9,9-bis[4-(2-acryloyloxyethoxy)phenyl]fluorene. In view of mechanical strength after curing, more preferred are 2,2-bis[4-[3-acryloyloxy-2-hydroxypropoxy]phenyl]propane having a bisphenol A skeleton, 2,2-bis[4-(3-methacryloyloxy-2-hydroxypropoxy)phenyl]propane, 2,2-bis[4-(meth)acryloyloxyethoxyphenyl] propane, and 2,2-bis[4-methacryloyloxypolyethoxyphenyl] propane (the average addition number of moles of an ethoxy group is 2.6 (commonly known as "D2.6E")).

Examples of an alicyclic ring in the alicyclic compound (A-2) having an alicyclic ring include cyclopentane, cyclohexane, cycloheptane, dicyclodecane, tricyclodecane, adamantane, and isobornyl. Examples of the alicyclic compound (A-2) having an alicyclic ring include 1,4-cyclohexane dimethanol di(meth)acrylate, tricyclodecane dimethanol di(meth)acrylate, adamantyl di(meth)acrylate, and adamantyl tri(meth)acrylate.

Examples of a heterocyclic ring in the compound (A-3) having a heterocyclic ring include: a heterocyclic ring containing only a nitrogen atom as a heteroatom such as triazine, carbazole, pyrozirin, or piperidine; a heterocyclic ring containing only an oxygen atom as a heteroatom such as tetrahydrofuran, oxane, dioxane, or dioxolane; a heterocyclic ring containing an oxygen atom and a nitrogen atom as a heteroatom such as morpholine; a heterocyclic ring containing only a sulfur atom as a heteroatom such as tetrahydrothiophene or tetrahydrothiopyran; and a heterocyclic ring containing a sulfur atom and a nitrogen atom as a heteroatom such as thiazine or thiazole. Examples of the compound (A-3) having a heterocyclic ring include ethoxylated isocyanuric acid tri(meth)acrylate, ε-caprolactone-modified tris(2-(meth)acryloyloxyethyl)isocyanurate, and hydroxypivaldehyde-modified trimethylolpropane di(meth)acrylate. One preferred embodiment is a dental restorative curable composition that is essentially free of a compound (A-3) having a heterocyclic ring and having a polymerizable functional group. Another preferred embodiment is a dental restorative curable composition that is essentially free of a compound having a heterocyclic ring that contains a nitrogen atom and having a polymerizable functional group. The heterocyclic ring containing a nitrogen atom includes a heterocyclic ring containing only a nitrogen atom as the heteroatom, a heterocyclic ring containing an oxygen atom and a nitrogen atom as the heteroatom, and a heterocyclic ring containing a sulfur atom and a nitrogen atom as the heteroatom. The expression "essentially free of a compound having a heterocyclic ring that contains a nitrogen atom and having a polymerizable functional group" means that the content of a compound having a heterocyclic ring that contains a nitrogen atom and having a polymerizable functional group in a dental restorative curable composition is less than 0.1 mass %, preferably less than 0.05 mass %, more preferably less than 0.01 mass %, and even more preferably less than 0 mass %. The expression "essentially free of a compound (A-3) having a heterocyclic ring and having a polymerizable functional group" means being free of a compound (A-3) having a heterocyclic ring and having a polymerizable functional group, in the same amount as the above.

The (meth)acrylic acid ester compound (A) preferably comprises a compound having no hydrogen bonding site in view of being able to suppress a decrease in mechanical strength due to water absorption through hydrogen bonding and having a higher water resistance. Specifically, the (meth) acrylic acid ester compound (A) preferably comprises a compound having a hydroxy group, a carboxy group, a primary amino group, a secondary amino group, an amide group, a urea bond, and a urethane bond, more preferably comprises a compound having none of a hydroxy group, a carboxy group, a primary amino group, a secondary amino group, an amide group, a urea bond, and a urethane bond and having a ring structure, even more preferably comprises a compound having none of a hydroxy group, a carboxy group, a primary amino group, a secondary amino group, an amide group, a urea bond, and a urethane bond and having an aromatic ring, and particularly preferably comprises a compound having none of a hydroxy group, a carboxy group, primary amino group, a secondary amino group, an amide group, a urea bond, and a urethane bond and having a bisphenol A skeleton. One preferred embodiment is a dental restorative curable composition in which a compound (A-1) having an aromatic ring comprises a compound having none of a hydroxy group, a carboxy group, primary amino group, a secondary amino group, an amide group, a urea bond, and a urethane bond and having an aromatic ring.

In view of paste handling properties and mechanical strength after curing, the weight-average molecular weight (Mw) of the (meth)acrylic acid ester compound (A) is preferably 500 to 50,000, more preferably 750 to 30,000, and even more preferably 1,000 to 15,000.

In a dental restorative curable composition of the present invention, the content of the (meth)acrylic acid ester compound (A) with respect to the total amount of the (meth) acrylic acid ester compound (A) and the mono(meth)acrylic acid ester compound (B) is preferably 10 to 99 mass %, and in view of further improving the mechanical strength, the water resistance, and the paste handling properties, is more preferably 30 to 95 mass % and even more preferably 50 to 90 mass %.

[Mono(Meth)Acrylic Acid Ester Compound (B)]

In a dental restorative curable composition of the present invention, the mono(meth)acrylic acid ester compound (B) can lower the viscosity of the dental restorative curable composition, and is used to impart excellent paste handling properties and impart high mechanical strength and water resistance to its cured product. The mono(meth)acrylic acid ester compound (B) may comprise at least one selected from the group consisting of a mono(meth)acrylic acid ester compound (B-1) represented by the above general formula (I) (hereinafter, referred to also as "mono(meth)acrylic acid ester compound (B-1)") and a mono(meth)acrylic acid ester compound (B-2) represented by the above general formula (II) (hereinafter, referred to also as "mono(meth)acrylic acid ester compound (B-2)"). The following describes the mono (meth)acrylic acid ester compound (B-1) and the mono (meth)acrylic acid ester compound (B-2). In the mono(meth) acrylic acid ester compound (B), the skeleton represented by the above general formula (I) and the skeleton represented by the above general formula (II) exhibit rigidity and hydrophobicity, and accordingly the dental restorative curable composition obtained exhibits low water absorption in the form of a cured product and a decrease in mechanical strength can be suppressed.

The symbols in formula (I) are described below. In formula (I), $R^1$ is a group represented by the above general formula (i) or a group represented by the above general formula (ii). In view of improving the curability of the dental restorative curable composition obtained, $R^4$ and $R^6$ in formula (i) or (ii) each independently represent a hydrogen atom or a methyl group. $R^3$ and $R^5$ each independently represent a divalent hydrocarbon group having 1 to 10 carbon atoms. In view of good paste handling properties of the dental restorative curable composition obtained and excellent mechanical strength after curing, the hydrocarbon group has preferably 1 to 6 carbon atoms, more preferably 1 to 4 carbon atoms, and even more preferably 1 to 3 carbon atoms. Examples of the hydrocarbon group include a linear or branched alkylene group having 1 to 10 carbon atoms; a cycloalkylene group having 3 to 10 carbon atoms; and a phenylene group. The symbols k and l each independently represent an integer of 0 to 6. In view of lowering the viscosity of the dental restorative curable composition, being capable of suppressing air bubble generation in its cured product, and improving the curability, the symbol k is preferably 0 to 4, more preferably 0 to 3, even more preferably 0 to 2, and particularly preferably 0 or 1. The symbol l is preferably 0 to 4, more preferably 0 to 2, and even more preferably 0 or 1.

Examples of the mono(meth)acrylic acid ester compound (B-1) include o-phenylphenol(meth)acrylate, m-phenylphenol(meth)acrylate, p-phenylphenol(meth)acrylate, methoxylated-o-phenylphenol(meth)acrylate, methoxylated-m-phenylphenol(meth)acrylate, methoxylated-p-phenylphenol (meth)acrylate, ethoxylated-o-phenylphenol(meth)acrylate, ethoxylated-m-phenylphenol(meth)acrylate, ethoxylated-p- phenylphenol(meth)acrylate, propoxylated-o-phenylphenol (meth)acrylate, propoxylated-m-phenylphenol(meth)acrylate, propoxylated-p-phenylphenol(meth)acrylate, butoxylated-o-phenylphenol(meth)acrylate, butoxylated-m-phenylphenol(meth)acrylate, and butoxylated-p-phenylphenol(meth)acrylate. These may be used alone, or two or more thereof may be used in combination. In view of good paste handling properties of the dental restorative curable composition obtained and its excellent mechanical strength after curing, the mono(meth)acrylic acid ester compound (B-1) is more preferably ethoxylated-o-phenylphenol acrylate, ethoxylated-m-phenylphenol acrylate, ethoxylated-p-phenylphenol acrylate, propoxylated-o-phenylphenol acrylate, propoxylated-m-phenylphenol acrylate, or propoxylated-p-phenylphenol acrylate, even more preferably ethoxylated-o-phenylphenol acrylate, ethoxylated-m-phenylphenol acrylate, or ethoxylated-p-phenylphenol acrylate, particularly preferably ethoxylated-o-phenylphenol acrylate or ethoxylated-m-phenylphenol acrylate, and most preferably ethoxylated-o-phenylphenol acrylate.

The symbols in formula (II) are described below. In formula (II), X is a divalent hydrocarbon group having 1 to 6 carbon atoms, or an oxygen atom. In view of good paste handling properties of the dental restorative curable composition obtained and its excellent mechanical strength after curing, X is preferably an oxygen atom. $R^2$ is a group represented by the above general formula (i) or a group represented by the general formula (ii). In view of good paste handling properties of the dental restorative curable composition obtained and its excellent mechanical strength after curing, $R^4$ and $R^6$ in formula (i) or (ii) each independently represent a hydrogen atom or a methyl group. $R^3$ and $R^5$ each independently represent a divalent hydrocarbon group having 1 to 10 carbon atoms. In view of good paste handling properties of the dental restorative curable composition obtained and its excellent mechanical strength after curing, the hydrocarbon group preferably has 1 to 6 carbon atoms, more preferably 1 to 4 carbon atoms, and even more preferably 1 to 3 carbon atoms. Examples of the hydrocarbon group include a linear or branched alkylene group having 1 to 10 carbon atoms; a cycloalkylene group having 3 to 10 carbon atoms; and a phenylene group. The symbols k and l each independently represent an integer of 0 to 6. In view of good paste handling properties of the dental restorative curable composition obtained and its excellent mechanical strength after curing, the symbol k is preferably 0 to 4, more preferably 0 to 3, even more preferably 0 to 2, and particularly preferably 0 or 1. The symbol l is preferably 0 to 4, more preferably 0 to 2, and even more preferably 0 or 1. One preferred embodiment is a dental restorative curable composition in which a mono(meth)acrylic acid ester compound (B) comprises a mono(meth)acrylic acid ester compound (B-2) represented by the general formula (II). Another preferred embodiment is a dental restorative curable composition in which a mono(meth)acrylic acid ester compound (B) comprises a mono(meth)acrylic acid ester compound (B-2) represented by the general formula (II), X is an oxygen atom, and $R^2$ is a group represented by the general formula (i). Still another preferred embodiment is a dental restorative curable composition in which a mono(meth)acrylic acid ester compound (B) comprises a mono(meth)acrylic acid ester compound (B-2) represented by the general formula (II), X is an oxygen atom, $R^2$ is a group represented by the general formula (i), and k is 0 or 1.

Examples of the mono(meth)acrylic acid ester compound (B-2) include o-phenoxybenzyl(meth)acrylate, m-phenoxybenzyl(meth)acrylate, p-phenoxybenzyl(meth)acrylate, 2-(o-phenoxyphenyl)ethyl(meth)acrylate, 2-(m-phenoxyphenyl)ethyl(meth)acrylate, 2-(p-phenoxyphenyl)ethyl(meth)acrylate, 3-(o-phenoxyphenyl)propyl(meth)acrylate, 3-(m-phenoxyphenyl)propyl(meth)acrylate, 3-(p-phenoxyphenyl)propyl(meth)acrylate, 4-(o-phenoxyphenyl)butyl(meth)acrylate, 4-(m-phenoxyphenyl)butyl(meth)acrylate, 4-(p-phenoxyphenyl)butyl(meth)acrylate, 5-(o-phenoxyphenyl)pentyl(meth)acrylate, 5-(m-phenoxyphenyl)pentyl(meth)acrylate, 5-(p-phenoxyphenyl)pentyl(meth)acrylate, 6-(o-phenoxyphenyl)hexyl(meth)acrylate, 6-(m-phenoxyphenyl)hexyl(meth)acrylate, and 6-(p-phenoxyphenyl)hexyl(meth)acrylate. These may be used alone, or two or more thereof may be used in combination. In view of good paste handling properties of the dental restorative curable composition obtained and its excellent mechanical strength after curing, the mono(meth)acrylic acid ester compound (B-2) is more preferably o-phenoxybenzyl acrylate, m-phenoxybenzyl acrylate, p-phenoxybenzyl acrylate, 2-(o-phenoxyphenyl)ethyl acrylate, 2-(m-phenoxyphenyl)ethyl acrylate, or 2-(p-phenoxyphenyl)ethyl acrylate, even more preferably o-phenoxybenzyl acrylate, m-phenoxybenzyl acrylate, or p-phenoxybenzyl acrylate, particularly preferably o-phenoxybenzyl acrylate or m-phenoxybenzyl acrylate, and most preferably m-phenoxybenzyl acrylate.

In a dental restorative curable composition of the present invention, the content of the mono(meth)acrylic acid ester compound (B) with respect to the total amount of the (meth)acrylic acid ester compound (A) and the mono(meth)acrylic acid ester compound (B) is preferably 1.0 to 90 mass %, and in view of further increasing the mechanical strength, the water resistance, and the paste handling properties, is more preferably 5 to 80 mass % and even more preferably 10 to 70 mass %.

The polymerizable monomer contained in the dental restorative curable composition of the present invention may consist essentially of only the (meth)acrylic acid ester compound (A) and the mono(meth)acrylic acid ester compound (B). A polymerizable monomer consisting essentially of only a (meth)acrylic acid ester compound (A) and a mono(meth)acrylic acid ester compound (B) means that the content of polymerizable monomers other than the (meth)acrylic acid ester compound (A) and the mono(meth)acrylic acid ester compound (B) is less than 10.0 mass %, preferably less than 5.0 mass %, more preferably less than 1.0 mass %, even more preferably less than 0.1 mass %, and particularly preferably less than 0.01 mass %, with respect to the total amount of the polymerizable monomers contained in the dental restorative curable composition.

[Inorganic Filler (C)]

The inorganic filler (C) in the present invention can be known inorganic particles used as fillers for dental composite resins, as long as the effects of the present invention are exhibited. Examples of the inorganic particles include various types of glasses (for example, glasses containing boron and/or aluminum and various heavy metals with the main component silicon dioxide (e.g., quartz, fused quartz, silica gel) or silicon), alumina, various types of ceramics, diatomaceous earth, kaolin, clay minerals (e.g., montmorillonite), activated earth, synthetic zeolite, mica, silica, calcium fluoride, ytterbium fluoride, calcium phosphate, barium sulfate, zirconium dioxide (zirconia), titanium dioxide (titania), and hydroxyapatite. The inorganic fillers may be used alone, or two or more thereof may be used in combination.

Important physical properties desired for dental materials include transparency and radiopacity similar to those of natural teeth. Among these properties, the transparency can be achieved by matching a refractive index of an inorganic filler (C) and a refractive index of a polymer of a polymerizable monomer as closely as possible. Meanwhile, the radiopacity can be imparted by using, as the inorganic filler (C), an inorganic filler containing a heavy metal element such as zirconium, barium, titanium, lanthanum, or strontium (oxide or the like). Such an inorganic filler containing a heavy metallic element typically has a high refractive index within a range of 1.5 to 1.6. In the present invention, for example, a cured product of a (meth)acrylic acid ester compound (A) having two or more (meth)acryloyloxy groups in one molecule, which constitutes a polymerizable monomer forming a polymer, and a mono(meth)acrylic acid ester compound (B) has a refractive index typically within a range of 1.5 to 1.6. Thus, even combination with such a radiopaque inorganic filler having a high refractive index allows an adjustment to reduce a difference in refractive index, thereby improving transparency of the resulting dental material.

Examples of the high-refractive-index inorganic fillers capable of imparting radiopacity include barium borosilicate glass (for example, "E-3000" manufactured by Esstech Inc., and "8235", "GM27884", and "GM39923" manufactured by Schott), strontium boroaluminosilicate glass (for example, "E-4000" manufactured by Esstech Inc., and "G018-093" and "GM32087" manufactured by Schott), lanthanum glass (for example, "GM31684" manufactured by Schott), fluoroaluminosilicate glass (for example, "G018-091" and "G018-117" manufactured by Schott), zirconia-containing glass (for example, "G018-310" and "G018-159" manufactured by Schott), strontium-containing glass (for example, "G018-163", "G018-093", and "GM32087" manufactured by Schott), zinc oxide-containing glass (for example, "G018-161" manufactured by Schott), and calcium-containing glass (for example, "G018-309" manufactured by Schott).

The inorganic filler (C) is not limited to have any particular shape, and can have any of a variety of shapes such as a crushed shape, a sheet shape, a flake shape, a fiber shape (short-fiber shape or long-fiber shape), a needle shape, a whisker shape, and a spherical shape. The inorganic filler (C) may have a shape that is a combination of different shapes among the above shapes, as long as the requirements of the present invention are satisfied.

It is important that the average primary particle diameter of the inorganic filler (C) in the present invention be 0.01 to 5 μm. By using the inorganic filler (C) having an average primary particle diameter in the range, it is possible to obtain a dental restorative curable composition that is excellent in polishability in the form of a cured product. In view of this, the average primary particle diameter of the inorganic filler (C) is preferably 0.02 μm or more, more preferably 0.04 μm or more, and is preferably 3 μm or less, and more preferably 2 μm or less. An average primary particle diameter of less than 0.01 μm tends to impair the mechanical strength, and an average primary particle diameter of more than 5 μm might impair the polishability.

The average primary particle diameter of the inorganic filler (C) can be determined by using a laser diffraction scattering method or electron microscopy on particles. Specifically, the laser diffraction scattering method is convenient for measuring the particle diameter of particles of 0.1 μm or more, and the electron microscopy is convenient for measuring the particle diameter of particles of less than 0.1 μm. The laser diffraction scattering method may be adopted for determining whether or not the average primary particle diameter is 0.1 μm or more.

According to the laser diffraction scattering method, the average primary particle diameter can be determined by, for example, performing measurement using a laser diffraction particle size distribution analyzer (for example, "SALD-2300" manufactured by Shimadzu Corporation) may be used with a 0.2% sodium hexametaphosphate aqueous solution as dispersion medium.

According to the electron microscopy, the average primary particle diameter can be determined by, for example, taking a micrograph of particles with a scanning electron microscope (SEM; for example, "SU3500H-800NA" manufactured by Hitachi High-Technologies Corporation), and measuring the particle diameter of particles (200 particles or more) observed in a unit field of view in the SEM image with image-analyzing particle size distribution measurement software (for example, "Macview" manufactured by Mountech Co., Ltd.). Here, the particle diameter of a particle is determined as a circle-equivalent diameter corresponding to the diameter of a circle having the same area as the particle. The average primary particle diameter is calculated from the number of particles and their particle diameters.

The content of the inorganic filler (C) in the dental restorative curable composition of the present invention is not particularly limited, and is preferably 50 to 95 mass %, more preferably 55 to 90 mass %, and even more preferably 60 to 85 mass %, with respect to the total amount of the dental restorative curable composition.

The inorganic filler (C) in the present invention is preferably one subjected to a surface treatment with a surface treatment agent in advance. By using the surface-treated inorganic filler (C), it is possible to further improve the mechanical strength of the resulting dental restorative curable composition after curing. In the case where two or more types of inorganic fillers (C) are used, only one type of them may be subjected to a surface treatment, or all types of them may be subjected to a surface treatment. In the latter case, the inorganic fillers (C) that have been individually subjected to a surface treatment may be mixed together, or a plurality of inorganic fillers that have been mixed together in advance may be collectively subjected to a surface treatment.

The surface treatment agent can be a known surface treatment agent. Examples of the surface treatment agent include: organometallic compounds such as organosilicon compounds, organotitanium compounds, organozirconium compounds, and organoaluminum compounds; and acidic group-containing organic compounds having at least one acidic group such as a phosphoric acid group, a pyrophosphoric acid group, a thiophosphoric acid group, a phosphonic acid group, a sulfonic acid group, or a carboxylic acid group. In the case where two or more surface treatment agents are used, the resulting surface treatment layer may be composed of a mixture of the two or more surface treatment agents, or may have a multilayer structure of a plurality of surface treatment layers. A known method for surface treatment may be used without particular limitation.

Examples of the organosilicon compounds include compounds represented by $R^7{}_n SiY_{(4-n)}$ (where $R^7$ is a substituted or unsubstituted hydrocarbon group having 1 to 12 carbon atoms, Y is an alkoxy group having 1 to 4 carbon atoms, an acetoxy group, a hydroxy group, a halogen atom, or a hydrogen atom, and n is an integer of 0 to 3, where $R^7$ may be the same or different when a plurality of $R^7$ exists, and Y may be the same or different when a plurality of Y exists).

Specific examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl) ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-β(aminoethyl)-γ-aminopropylmethyldimethoxysilane, N-β(aminoethyl)-γ-aminopropyltrimethoxysilane, N-β(aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane [having 3 to 12 carbon atoms between the (meth)acryloyloxy group and the silicon atom; e.g., γ-methacryloyloxypropyltrimethoxysilane], and ω-(meth)acryloyloxyalkyltriethoxysilane [having 3 to 12 carbon atoms between the (meth)acryloyloxy group and the silicon atom; e.g., γ-methacryloyloxypropyltriethoxysilane]. In the present invention, the expression "(meth)acryloyloxy" is used to include both methacryloyloxy and acryloyloxy.

Preferred are silane coupling agents having a functional group that is copolymerizable with the polymerizable monomer. Examples of such coupling agents include ω-(meth)acryloyloxyalkyltrimethoxysilane [having 3 to 12 carbon atoms between the (meth)acryloyloxy group and the silicon atom], ω-(meth)acryloyloxyalkyltriethoxysilane [having 3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

Examples of the organotitanium compounds include tetramethyl titanate, tetraisopropyl titanate, tetra-n-butyl titanate, butyl titanate dimmer, and tetra(2-ethylhexyl)titanate.

Examples of the organozirconium compounds include zirconium isopropoxide, zirconium-n-butoxide, zirconium acetylacetonate, and zirconyl acetate.

Examples of the organoaluminum compounds include aluminum acetylacetonate, and a chelate compound of a salt of aluminum and an organic acid.

Examples of the acidic group-containing organic compounds containing a phosphate group include 2-ethylhexyl acid phosphate, stearyl acid phosphate, 2-(m eth)acryloyloxyethyl dihydrogen phosphate, 3-(m eth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(m eth)acryloyloxyheptyl dihydrogen phosphate, 8-(meth)acryloyloxyoctyl dihydrogen phosphate, 9-(m eth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth) acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, ammonium salts, etc. thereof.

The acidic group-containing organic compounds having an acidic group such as a pyrophosphate group, a thiophosphate group, a phosphonate group, a sulfonate group, or a carboxylate group can be suitably selected from those described in for example WO 2012/042911.

The surface treatment agent may be used alone, or two or more thereof may be used in combination. Also, to increase the chemical bonding properties between the inorganic filler (C) and the polymerizable monomer thereby to improve the mechanical strength of a cured product, it is more preferable to use an acidic group-containing organic compound that is copolymerizable with the polymerizable monomer.

The used amount of the surface treatment agent is not particularly limited, and is for example preferably 0.1 to 50 parts by mass with respect to 100 parts by mass of the inorganic filler (C).

[Polymerization Initiator (D)]

The following describes a polymerization initiator (D). The polymerization initiator (D) includes a thermal polymerization initiator, a photopolymerization initiator, and a chemical polymerization initiator. These may be used alone, or two or more thereof may be used in combination.

Examples of the thermal polymerization initiator include organic peroxides and azo compounds.

Examples of the organic peroxides include ketone peroxide, hydroperoxide, diacyl peroxide, dialkyl peroxide, peroxyketal, peroxyester, and peroxydicarbonate.

Examples of the ketone peroxide include methyl ethyl ketone peroxide, methyl isobutyl ketone peroxide, methyl cyclohexanone peroxide, and cyclohexanone peroxide.

Examples of the hydroperoxide include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxide include acetyl peroxide, isobutyryl peroxide, benzoyl peroxide, decanoyl peroxide, 3,5,5-trimethylhexanoylperoxide, 2,4-dichlorobenzoyl peroxide, and lauroyl peroxide.

Examples of the dialkyl peroxide include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl-4,4-bis(t-butylperoxy)valerate.

Examples of the peroxyester include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butylperoxyhexahydroterephthalate, t-butylperoxy-3,3,5-trimethylhexanoate, t-butylperoxyacetate, t-butylperoxybenzoate, and t-butylperoxymaleic acid.

Examples of the peroxydicarbonate include di-3-methoxyperoxydicarbonate, di(2-ethylhexyl)peroxydicarbonate, bis(4-t-butylcyclohexyl)peroxydicarbonate, diisopropyl peroxydicarbonate, di-n-propyl peroxydicarbonate, di(2-ethoxyethyl)peroxydicarbonate, and diallyl peroxydicarbonate.

Among these organic peroxides, the diacyl peroxides are preferably used in view of the overall balance among safety, storage stability, and radical generation capability. Among the diacyl peroxides, benzoyl peroxide is more preferably used.

Examples of the azo compounds include 2,2'-azobis (isobutyronitrile), 2,2'-azobis(2,4-dimethylvaleronitrile), 4,4'-azobis(4-cyanovaleric acid), 1,1'-azobis(cyclohexane-1-carbonitrile), dim ethyl-2,2'-azobis(isobutyrate), and 2,2'-azobis(2-amidinopropane)dihydrochloride.

Examples of the photopolymerization initiator include (bis)acylphosphine oxides, α-diketones, and coumarins.

Examples of acylphosphine oxides among the (bis)acylphosphine oxides include 2,4,6-trimethylbenzoyl diphenylphosphine oxide, 2,6-dimethoxybenzoyl diphenylphosphine oxide, 2,6-dichlorobenzoyl diphenylphosphine oxide, 2,4,6-trimethylbenzoyl methoxyphenylphosphine oxide, 2,4,6-trimethylbenzoyl ethoxyphenylphosphine oxide, 2,3,5,6-tetramethylbenzoyl diphenylphosphine oxide, benzoyl di(2,6-dimethylphenyl)phosphonate, and salts thereof. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphineoxide, and salts thereof.

Among these (bis)acylphosphine oxides, preferred are 2,4,6-trimethylbenzoyl diphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Example of the α-diketones include diacetyl, benzyl, camphorquinone, 2,3-pentadione, 2,3-octadione, 9,10-phenanthrenequinone, 4,4'-oxybenzyl, and acenaphthenequinone. Among these, camphorquinone is preferable.

Examples of the coumarins include compounds disclosed in JP 9(1997)-3109 A and JP 10(1998)-245525 A, such as 3,3'-carbonylbis(7-diethylaminocoumarin), 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-m ethoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-m ethoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazole-2-ylidene)acetyl]coumarin, 3-[(1-methylnaphtho[1,2-d]thiazole-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H,5H,11H-[1]benzopyrano[6,7,8-ij]quinolizin-11-one.

Among the coumarins, preferred are 3,3'-carbonylbis(7-diethylaminocoumarin) and 3,3'-carbonylbis(7-dibutylaminocoumarin).

Among these photopolymerization initiators, at least one selected from the group consisting of (bis)acylphosphine oxides, α-diketones, and coumarins that are widely used for dentistry is preferably used.

As necessary, combination of the photopolymerization initiator with a polymerization accelerator may allow more efficient photopolymerization in a shorter time.

Examples of polymerization accelerators suitable for the photopolymerization initiator include tertiary amines, aldehydes, thiol group-containing compounds, sulfinic acids and salts thereof, borate compounds, and triazine compounds. In addition, the polymerization accelerators may be used alone, or two or more thereof may be used in combination. One preferred embodiment is a dental restorative curable composition in which a polymerization initiator (D) comprises a photopolymerization initiator, and further comprises a polymerization accelerator for the photopolymerization initiator, and the polymerization accelerator is a tertiary amine.

Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N, N-bis(2-hydroxyethyl)-3,5-dimethylaniline, N, N-di(2-hydroxyethyl)-p-toluidine, N, N-bis(2-hydroxyethyl)-3,4-dimethylaniline, N, N-bis(2-hydroxyethyl)-4-ethylaniline, N,N-bis(2-hydroxyethyl)-4-isopropylaniline, N,N-bis(2-hydroxyethyl)-4-t-butylaniline, N, N-bis(2-hydroxyethyl)-3,5-diisopropylaniline, N,N-bis(2-hydroxyethyl)-3,5-di-t-butylaniline, n-butoxyethyl 4-(N,N-dimethylamino)benzoate, (2-methacryloyloxy)ethyl 4-(N,N-dimethylamino)benzoate, ethyl 4-(N,N-dimethylamino)benzoate, butyl 4-(N,N-dimethylamino)benzoate, N-methyldiethanolamine, N-4-(N,N-dimethylamino)benzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

Examples of the aldehydes include dimethylaminobenzaldehyde and terephthalaldehyde. Examples of the thiol group-containing compounds include 2-mercaptobenzoxazole, decanethiol, 3-mercaptopropyltrimethoxysilane, and thiobenzoic acid.

Examples of the sulfinic acids and salts thereof include benzenesulfinic acid, sodium benzenesulfinate, potassium benzenesulfinate, calcium benzenesulfinate, lithium benzenesulfinate, p-toluenesulfinic acid, p-sodium toluenesulfinate, p-potassium toluenesulfinate, p-calcium toluenesulfinate, p-lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, and calcium 2,4,6-triisopropylbenzenesulfinate.

A preferably used chemical polymerization initiator is a redox polymerization initiator such as organic peroxides and amines; organic peroxides, amines, and sulfinic acids (or salts thereof). The use of such a redox polymerization initiator requires that an oxidizing agent and a reducing agent should be packed separately and mixed together immediately before use. Examples of the oxidizing agent for the redox polymerization initiator include organic peroxides. The organic peroxides as the oxidizing agent for the redox polymerization initiator are not particularly limited, and known organic peroxides may be used. Specific examples of the organic peroxides include the organic peroxides exemplified above for the thermal polymerization initiator.

Among these organic peroxides, the diacyl peroxides are preferably used in view of the overall balance among safety, storage stability, and radical generation capability. Among the diacyl peroxides, benzoyl peroxide is more preferably used.

Typically used reducing agents for the redox polymerization initiator are aromatic tertiary amines having no electron withdrawing group in an aromatic ring. Examples of the aromatic tertiary amines having no electron withdrawing group in an aromatic ring include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N, N-bis(2-hydroxyethyl)-4-ethylaniline, N, N-bis(2-hydroxyethyl)-4-isopropylaniline, N,N-bis(2-hydroxyethyl)-4-t-butylaniline, N,N-bis(2-hydroxyethyl)-3,5-diisopropylaniline, and N,N-bis(2-hydroxyethyl)-3,5-di-t-butylaniline.

The chemical polymerization initiator may be used in combination with a polymerization accelerator as necessary. The polymerization accelerator for the chemical polymerization initiator may be selected for use among polymerization accelerators commonly used in industry. Particularly, a polymerization accelerator for dentistry is preferably used. Also, the polymerization accelerator may be used alone, or two or more thereof may be used in combination. Specific examples of the polymerization accelerator for the chemical polymerization initiator include amines, sulfinic acids and salts thereof, copper compounds, tin compounds, derivatives of barbituric acid, and vanadium compounds. One preferred embodiment is a dental restorative curable composition in which a polymerization initiator (D) comprises a chemical polymerization initiator, and further comprises a polymerization accelerator for the chemical polymerization initiator, and the polymerization accelerator is an amine.

The amines used as the polymerization accelerator for the chemical polymerization initiator are classified into aliphatic amines and aromatic amines having an electron withdrawing group in an aromatic ring. Examples of the aliphatic amines include: aliphatic primary amines such as n-butylamine, n-hexylamine, and n-octylamine; aliphatic secondary amines such as diisopropylamine, dibutylamine, and N-methylethanolamine; and aliphatic tertiary amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, the aliphatic tertiary amines are preferable in view of curability and storage stability of the composition. Among the aliphatic tertiary amines, N-methyldiethanolamine and triethanolamine are more preferably used.

Examples of the aromatic tertiary amines having an electron withdrawing group in an aromatic ring that are used as a polymerization accelerator for the chemical polymerization initiator include ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-N,N-dimethylaminobenzoate, 4-(N,N-dimethylamino) benzophenone, and butyl 4-(N,N-dimethylamino)benzoate. Among these, at least one selected from the group consisting of N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone is preferably used in view of capability of imparting an excellent curability to the composition.

The sulfinic acid and salts thereof used as the polymerization accelerator include those exemplified above as the polymerization accelerator for the photopolymerization initiator. Sodium benzenesulfinate, sodium p-toluenesulfinate, and sodium 2,4,6-triisopropylbenzenesulfinate are preferable.

Examples of the copper compounds that are suitably used as the polymerization accelerator include copper acetylacetonate, copper(II) acetate, copper oleate, copper(II) chloride, and copper(II) bromide.

Examples of the tin compounds used as the polymerization accelerator include di-n-butyltin dimaleate, di-n-octyltin dimaleate, di-n-octyltin dilaurate, and di-n-butyltin dilaurate. Particularly suitable tin compounds are di-n-octyltin dilaurate and di-n-butyltin dilaurate.

Among these, for dental composite resins, a photopolymerization initiator is preferably used for the convenience of curing in the oral cavity, while for dental mill blanks, a thermal polymerization initiator is preferably used for increasing the degree of polymerization to improve the strength.

The content of the polymerization initiator (D) in the present invention is not particularly limited. However, in view of the curability and the like of the resulting composition, the content of the polymerization initiator (D) is preferably 0.001 to 30 parts by mass with respect to 100 parts by mass of the polymerizable monomer. In the case where the content of the polymerization initiator (D) is 0.001 parts by mass or more with respect to 100 parts by mass of the polymerizable monomer, polymerization proceeds sufficiently and thus there is no risk of decrease in mechanical strength. The content of the polymerization initiator (D) is more preferably 0.05 parts by mass or more, and even more preferably 0.1 parts by mass or more, with respect to 100 parts by mass of the polymerizable monomer. Meanwhile, in the case where the content of the polymerization initiator (D) is 30 parts by mass or less with respect to 100 parts by mass of the polymerizable monomer, a sufficient mechanical strength can be achieved even with a low polymerization performance exhibited by the polymerization initiator itself, and furthermore there is no risk of precipitation from a composition. The content of the polymerization initiator (D) is more preferably 20 parts by mass or less with respect to 100 parts by mass of the polymerizable monomer.

A dental restorative curable composition of the present invention may comprise a polymer, particularly a prepolymer, in view of reducing polymerization shrinkage stress. In addition, a dental composite resin is typically polymerized and cured by light irradiation. At curing, a polymerization shrinkage stress is applied to an adhesive interface between a cavity wall and the composite resin. In the case where the polymerization shrinkage stress is large, a contraction gap may be generated at the adhesive interface, causing secondary caries, dental pulp irritation, staining, detachment of a cured product, and the like. Accordingly, by combining with an effect of further reducing the polymerization shrinkage stress, a more preferable dental composite resin is considered to be achieved. In particular, in the case where the dental restorative curable composition of the present invention is used as a dental composite resin, the dental restorative curable composition of the present invention preferably comprises a polymer, particularly a prepolymer, in view of not only, in the form of a cured product, a high mechanical strength and excellent characteristics such as water resistance and polishability but also a more excellent reduction effect of polymerization shrinkage stress. Prepolymer refers to an intermediate of a polymerization reaction of a polymerizable monomer after the reaction is stopped at an appropriate point, or a polymer having a polymerizable functional group introduced therein after polymerization. In either case, the prepolymer has an unreacted polymerizable functional group that enables further polymerization. The prepolymer may be used alone, or two or more thereof may be used in combination.

[Prepolymer]

The unreacted polymerizable functional group in a prepolymer is not particularly limited. Examples of the unreacted polymerizable functional group include a carbon-carbon double bond, a vinyl group, a vinyloxy group, a (meth)allyl group, a (meth)acryloyl group, a maleoyl group, a styryl group, and a cinnamoyl group. The unreacted polymerizable functional group is preferably a (meth)acryloyl group, and more preferably a (meth)acryloyloxy group or a (meth)acrylamide group. The prepolymer has, on average, preferably at least 1, and more preferably at least 2 unreacted polymerizable functional groups per molecule, and is, to further improve the effect of reducing the polymerization shrinkage stress, even more preferably at least 5, and particularly preferably at least 10 unreacted polymerizable functional groups per molecule. The prepolymer may have, on average, at least 15, at least 20, or at least 25 unreacted polymerizable functional groups per molecule. The prepolymer has, on average, preferably at most 1,000, and more preferably at most 500 unreacted polymerizable functional groups per molecule, and is, to further improve the effect of reducing the polymerization shrinkage stress, even more preferably at most 100, and particularly preferably at most 50 unreacted polymerizable functional groups per molecule. The method used to measure the number of unreacted polymerizable functional groups in a prepolymer is not particularly limited. For example, the number of unreacted polymerizable functional groups can be determined by measuring the concentration (mol/g) of unreacted polymerizable functional groups in the prepolymer by NMR analysis, and multiplying the measured concentration by the weight-average molecular weight of the prepolymer, as will be described later. More specifically, the number of unreacted polymerizable functional groups can be determined by using the method described in the EXAMPLES section below.

The molecular weight of a prepolymer is not particularly limited. For advantages such as further enhancement of the effects of the present invention, the weight-average molecular weight of the prepolymer is preferably 1,000 or more, and is, to further improve the effect of reducing the polymerization shrinkage stress, more preferably 5,000 or more, and even more preferably 10,000 or more, and is preferably 1,000,000 or less, and is, to further improve the effect of reducing the polymerization shrinkage stress, more preferably 500,000 or less, even more preferably 300,000 or less, and particularly preferably 100,000 or less. The weight-average molecular weight of prepolymer may be 80,000 or less, or 60,000 or less. The method used to measure the weight-average molecular weight of a prepolymer is not particularly limited. For example, the weight-average molecular weight of a prepolymer can be measured by GPC, more specifically, the method described in the EXAMPLES section below.

The content of the prepolymer in the dental restorative curable composition of the present invention is not particularly limited. However, in view of consistency stability, polymerization shrinkage stress, and handling properties of the resulting dental restorative curable composition, and the mechanical strength and the like of the resulting cured product, the content of the prepolymer with respect to the mass of the dental restorative curable composition is preferably 0.5 mass % or more, more preferably 1 mass % or more, and even more preferably 3 mass % or more, and is preferably 20 mass % or less, more preferably 18 mass % or less, and even more preferably 16 mass % or less, and may be 12 mass % or less, or 8 mass % or less.

Aside from the above-mentioned components, a dental restorative curable composition of the present invention may further comprise a pH adjuster, an ultraviolet absorber, an antioxidant, a coloring agent (for example, pigment), a chain transfer agent, an antibacterial agent, an X-ray contrast agent, a thickener, a fluorescent agent or the like, depending on the purpose. These may be used alone or in combination of two or more thereof.

As the pigment, known pigments that are used in dental composite resins are used without any limitations. The pigment may be any of inorganic pigments and/or organic pigments. Examples of the inorganic pigments include: chromates such as chromium yellow, zinc yellow, and barium yellow; ferrocyanides such as iron blue; sulfides such as vermilion, cadmium yellow, zinc sulfide, and cadmium red; sulfates such as barium sulfate, zinc sulfate, and strontium sulfate; oxides such as antimony white, zinc flower, titanium white, red oxide, black iron, and chromium oxide; hydroxides such as aluminum hydroxide; silicates such as calcium silicate and lapis lazuli; and carbons such as carbon black and graphite. Examples of the organic pigments include: nitroso compounds such as Naphthol Green B and Naphthol Green Y; nitro pigments such as Naphthol Yellow S and Lithol Fast Yellow 2G; insoluble azo pigments such as Permanent Red 4R, Brilliant Fast Scarlet, Hansa Yellow, and Benzidine Yellow; poorly soluble azo pigments such as Lithol Red, Lake Red C, and Lake Red D; soluble azo pigments such as Brilliant Carmine 6B, Permanent Red F5R, Pigment Scarlet 3B, and Bordeaux 10B, phthalocyanine pigments such as Phthalocyanine Blue, Phthalocyanine Green, and Sky Blue; basic compounds such as Rhodamine Lake, Malachite Green Lake, and Methyl Violet Lake; and acidic compounds such as Peacock Blue Lake, Eosin Lake, and Quinoline Yellow Lake. These pigments may be used alone, or two or more thereof may be used in combination, which can be appropriately selected depending on intended color tones.

The content of the pigment in the dental restorative curable composition is appropriately adjusted depending on intended color tones, and thus is not particularly limited. The content of the pigment is preferably 0.000001 parts by mass or more, and more preferably 0.00001 parts by mass or more, and is preferably 5 parts by mass or less, and more preferably 1 part by mass or less, in 100 parts by mass of the dental restorative curable composition. The content of the pigment is preferably 0.000001 to 5 parts by mass, and more preferably 0.00001 to 1 part by mass, in 100 parts by mass of the dental restorative curable composition.

Examples of the chain transfer agent include mercaptan compounds (such as n-octyl mercaptan, n-dodecyl mercaptan, t-dodecyl mercaptan, hexadecyl mercaptan, and n-octadecyl mercaptan), halogen compounds (such as carbon tetrachloride, methylene chloride, and bromoform), unsaturated hydrocarbon compounds (such as 2,4-diphenyl-4-methyl-1-pentene, α-terpinene, dipentene, and terpinolene), thiols (such as mercaptoacetic acid, 2-ethylhexyl mercaptoacetate, 3-methoxybutyl mercaptoacetate, β-mercaptopropionic acid, methyl β-mercaptopropionate, 2-ethylhexyl β-mercaptopropionate, 3-methoxybutyl β-mercaptopropionate, 2-mercaptoethanol, and 3-mercapto-1,2-propanediol).

A method for producing a dental restorative curable composition of the present invention comprises, for example, the following steps (1) to (2).

(1) Kneading Step

A kneading step is a step of performing a kneading operation in which a (meth)acrylic acid ester compound (A), a mono(meth)acrylic acid ester compound (B), and a polymerization initiator (D) are put into a vessel of a kneading machine to prepare a polymerizable monomer-containing composition, and then an inorganic filler (C) is further put and kneading is performed to produce a pasty composition. In the kneading step, the kneading method is not particularly limited as long as the effects of the present invention are exhibited, and a known method may be adopted. In view of shortening the kneading time and preventing occurrence of variation in paste characteristics, the kneading is preferably performed while heating. The kneading temperature is preferably 40 to 60° C. Temperatures lower than 40° C. cannot sufficiently achieve the kneading time shortening effect, and temperatures higher than 60° C. might cause polymerization and curing or deterioration of the composition during the kneading. In addition, a vacuum defoaming treatment may be performed during the kneading as necessary. The degree of vacuum in this case is not particularly limited. To efficiently remove air bubbles, the degree of vacuum is preferably 5 to 200 Torr.

(2) Defoaming Step

A defoaming step is a step of performing a defoaming operation in which after the pasty composition is put into the vessel of the defoaming machine, defoaming is performed on the pasty composition by extruding the paste out of the vessel under pressure while removing air bubbles inside the paste by decompression. The defoaming conditions are not particularly limited. To efficiently remove air bubbles, the degree of vacuum is preferably 5 to 200 Torr in order to suppress separation of the polymerizable monomer-containing composition, which comprises the (meth)acrylic acid ester compound (A), the mono(meth)acrylic acid ester compound (B), and the polymerization initiator (D), and the inorganic filler (C). The decompression time is preferably 3 to 30 minutes. Also, the pressure at extrusion is preferably 0.5 to 5 MPa. The compression time is preferably 3 to 30 minutes. Further, a heat treatment can be performed during the defoaming as necessary. The temperature in this case is not particularly limited. To efficiently remove air bubbles, the temperature is preferably 40 to 60° C.

A dental restorative curable composition of the present invention is excellent in paste handling properties, and has a high mechanical strength and excellent water resistance and polishability in the form of a cured product, and accordingly can be suitably used as a dental material. Specifically, the dental restorative curable composition of the present invention can be suitably used as a dental material (particularly, a dental composite resin) that can serve as a substitute for part or the whole of a natural tooth in the field of dentistry. In addition, a cured product obtained by polymerizing and curing the dental restorative curable composition of the present invention can be suitably used as a dental mill blank that is a material to be milled for use in CAD/CAM systems in which a milling process is performed with a milling device. When used as a dental composite resin, the flexural modulus of the cured product of the dental restorative curable composition is preferably 8 GPa or more. When used as a dental mill blank, the flexural modulus of the cured product of the dental restorative curable composition is preferably 12 GPa or more. The flexural modulus of the cured product of the dental restorative curable composition is not particularly limited. However, an excessively high flexural modulus might cause damage such as wear or fracture on the tooth structure, and accordingly the flexural modulus may be 30 GPa or less.

EXAMPLES

The following describes the present invention in detail by way of Examples and Comparative Examples. However, the present invention is no way limited by the following Examples.

[(Meth)Acrylic Acid Ester Compound (A) Having Two or More (Meth)Acryloyloxy Groups Per Molecule]

D2.6E: 2,2-bis[4-methacryloyloxypolyethoxyphenyl]propane (the average addition number of moles of an ethoxy group is 2.6) (manufactured by SHIN-NAKAMURA CHEMICAL Co., Ltd.)

Bis-MEPP: 2,2-bis[4-[2-(methacryloyloxy)ethoxy]phenyl]propane (manufactured by SHIN-NAKAMURA CHEMICAL Co., Ltd.)

Bis-GMA: 2,2-bis[4-(3-methacryloyloxy-2-hydroxypropoxy)phenyl]propane (manufactured by SHIN-NAKAMURA CHEMICAL Co., Ltd.)

DCP: tricyclodecane dimethanol dimethacrylate (manufactured by SHIN-NAKAMURA CHEMICAL Co., Ltd.)

UDMA: [2,2,4-trimethylhexamethylenebis(2-carbamoyloxyethyl)]dimethacrylate (manufactured by Kyoeisha Chemical Co., Ltd.)

TEGDMA: triethylene glycol dimethacrylate (manufactured by SHIN-NAKAMURA CHEMICAL Co., Ltd.)

[Mono(Meth)Acrylic Acid Ester Compound (B)]

POBA: m-phenoxybenzyl acrylate (manufactured by Kyoeisha Chemical Co., Ltd.)

POBMA: m-phenoxybenzyl methacrylate (manufactured by Kyoeisha Chemical Co., Ltd.)

EPPA: ethoxylated-o-phenylphenol acrylate (manufactured by SHIN-NAKAMURA CHEMICAL Co., Ltd.)
[Mono(Meth)Acrylic Acid Ester Compound]
MMA: methyl methacrylate (manufactured by Kuraray Co., Ltd.)
IBMA: isobornyl methacrylate (manufactured by Kyoeisha Chemical Co., Ltd.)
DDMA: dodecyl methacrylate (manufactured by Kyoeisha Chemical Co., Ltd.)
[Mono(Meth)Acrylamide Compound]
HEAA: N-hydroxyethyl acrylamide
[Inorganic Filler (C)]
UF2.0: barium glass (average primary particle diameter of 2.0 μm, manufactured by Schott)
UF1.5: barium glass (average primary particle diameter of 1.5 μm, manufactured by Schott)
UF0.7: barium glass (average primary particle diameter of 0.7 μm, manufactured by Schott)
NF180: barium glass (average primary particle diameter of 0.180 μm, manufactured by Schott)
Ar130: fine silica particles (average primary particle diameter of 0.016 μm, manufactured by Nippon Aerosil Co., Ltd.)
Ox50: fine silica particles (average primary particle diameter of 0.04 μm, manufactured by Nippon Aerosil Co., Ltd.)
[Surface Treatment Agent]
γ-MPS: γ-methacryloyloxypropyltrimethoxysilane (manufactured by Shin-Etsu Chemical Co., Ltd.)
11-MUS: 11-methacryloyloxydodecyltrimethoxysilane (manufactured by Shin-Etsu Chemical Co., Ltd.)
[Surface-Treated Inorganic Filler]
Inorganic filler (C6): irregular silica-zirconia, product surface-treated with γ-methacryloyloxypropyltrimethoxysilane, average particle diameter: 4.2 μm, refractive index: 1.54
Inorganic filler (C7): spherical silica-zirconia, product surface-treated with γ-methacryloyloxypropyltrimethoxysilane, average particle diameter: 0.1 μm, refractive index: 1.52
[Polymerization Initiator (D)]
CQ: camphorquinone (photopolymerization initiator) (manufactured by Tokyo Chemical Industry Co., Ltd.)
TPO: 2,4,6-trimethylbenzoyl diphenylphosphine oxide (manufactured by BASF Japan Ltd.)
THP: 1,1,3,3-tetramethylbutyl hydroperoxide (thermal polymerization initiator) (manufactured by NOF CORPORATION)
BPO: benzoyl peroxide (thermal polymerization initiator) (manufactured by NOF CORPORATION)
[Polymerization Accelerator]
JJA: ethyl 4-(N,N-dimethylamino)benzoate
DEPT: N,N-bis(2-hydroxyethyl)-p-toluidine
[Chain Transfer Agent]
DPMP: 2,4-diphenyl-4-methyl-1-pentene (manufactured by Tokyo Chemical Industry Co., Ltd.)

Production Example 1 of Polymerizable Monomer-Containing Composition

A polymerizable monomer-containing composition (M1) was prepared by dissolving 0.2 parts by mass of CQ as a photopolymerization initiator, 0.25 parts by mass of TPO, and 0.3 parts by mass of JJA as a polymerization accelerator in 70 parts by mass of D2.6E and 30 parts by mass of POBA.

Production Example 2 of Polymerizable Monomer-Containing Composition

A polymerizable monomer-containing composition (M2) was prepared by dissolving 0.2 parts by mass of CQ as a photopolymerization initiator, 0.25 parts by mass of TPO, and 0.3 parts by mass of JJA as a polymerization accelerator in 90 parts by mass of D2.6E and 10 parts by mass of POBA.

Production Example 3 of Polymerizable Monomer-Containing Composition

A polymerizable monomer-containing composition (M3) was prepared by dissolving 0.2 parts by mass of CQ as a photopolymerization initiator, 0.25 parts by mass of TPO, and 0.3 parts by mass of JJA as a polymerization accelerator in 50 parts by mass of D2.6E and 50 parts by mass of POBA.

Production Example 4 of Polymerizable Monomer-Containing Composition

A polymerizable monomer-containing composition (M4) was prepared by dissolving 0.2 parts by mass of CQ as a photopolymerization initiator, 0.25 parts by mass of TPO, and 0.3 parts by mass of JJA as a polymerization accelerator in 70 parts by mass of D2.6E and 30 parts by mass of POBMA.

Production Example 5 of Polymerizable Monomer-Containing Composition

A polymerizable monomer-containing composition (M5) was prepared by dissolving 0.2 parts by mass of CQ as a photopolymerization initiator, 0.25 parts by mass of TPO, and 0.3 parts by mass of JJA as a polymerization accelerator in 70 parts by mass of D2.6E and 30 parts by mass of EPPA.

Production Example 6 of Polymerizable Monomer-Containing Composition

A polymerizable monomer-containing composition (M6) was prepared by dissolving 0.2 parts by mass of CQ as a photopolymerization initiator, 0.25 parts by mass of TPO, and 0.3 parts by mass of JJA as a polymerization accelerator in 70 parts by mass of Bis-MEPP and 30 parts by mass of POBA.

Production Example 7 of Polymerizable Monomer-Containing Composition

A polymerizable monomer-containing composition (M7) was prepared by dissolving 0.2 parts by mass of CQ as a photopolymerization initiator, 0.25 parts by mass of TPO, and 0.3 parts by mass of JJA as a polymerization accelerator in 70 parts by mass of Bis-GMA and 30 parts by mass of POBA.

Production Example 8 of Polymerizable Monomer-Containing Composition

A polymerizable monomer-containing composition (M8) was prepared by dissolving 0.2 parts by mass of CQ as a photopolymerization initiator, 0.25 parts by mass of TPO, and 0.3 parts by mass of JJA as a polymerization accelerator in 70 parts by mass of DCP and 30 parts by mass of POBA.

Production Example 9 of Polymerizable Monomer-Containing Composition

A polymerizable monomer-containing composition (M9) was prepared by dissolving 0.2 parts by mass of CQ as a photopolymerization initiator, 0.25 parts by mass of TPO, and 0.3 parts by mass of JJA as a polymerization accelerator in 70 parts by mass of D2.6E and 30 parts by mass of TEGDMA.

Production Example 10 of Polymerizable Monomer-Containing Composition

A polymerizable monomer-containing composition (M10) was prepared by dissolving 2 parts by mass of BPO as a thermal polymerization initiator and 2 parts by mass of DEPT as a polymerization accelerator in 40 parts by mass of D2.6E, 30 parts by mass of Bis-GMA, and 30 parts by mass of TEGDMA.

Production Example 11 of Polymerizable Monomer-Containing Composition

A polymerizable monomer-containing composition (M11) was prepared by dissolving 1 part by mass of CQ as a photopolymerization initiator, 1.25 parts by mass of TPO, and 1.5 parts by mass of JJA as a polymerization accelerator in 70 parts by mass of D2.6E, 30 parts by mass of TEGDMA, and 4 parts by mass of HEAA.

Production Example 12 of Polymerizable Monomer-Containing Composition

A polymerizable monomer-containing composition (M12) was prepared by dissolving 0.2 parts by mass of CQ as a photopolymerization initiator, 0.25 parts by mass of TPO, and 0.3 parts by mass of JJA as a polymerization accelerator in 70 parts by mass of D2.6E and 30 parts by mass of MMA.

Production Example 13 of Polymerizable Monomer-Containing Composition

A polymerizable monomer-containing composition (M13) was prepared by dissolving 0.5 parts by mass of THP as a thermal polymerization initiator and 1.5 parts by mass of JJA as a polymerization accelerator in 70 parts by mass of D2.6E and 30 parts by mass of POBA.

Production Example 14 of Polymerizable Monomer-Containing Composition

A polymerizable monomer-containing composition (M14) was prepared by dissolving 1.5 parts by mass of BPO as a thermal polymerization initiator and 1.5 parts by mass of JJA as a polymerization accelerator in 70 parts by mass of UDMA and 30 parts by mass of TEGDMA.

The compositions of the polymerizable monomer-containing compositions are shown in Table 1 below.

TABLE 1

| Component (parts by mass) | M1 | M2 | M3 | M4 | M5 | M6 | M7 | M8 | M9 | M10 | M11 | M12 | M13 | M14 |
|---|---|---|---|---|---|---|---|---|---|---|---|---|---|---|
| (Meth)acrylic acid ester compound (A) | | | | | | | | | | | | | | |
| D2.6E | 70 | 90 | 50 | 70 | 70 | | | | 70 | 40 | 70 | 70 | 70 | |
| Bis-MEPP | | | | | | 70 | | | | | | | | |
| Bis-GMA | | | | | | | 70 | | | 30 | | | | |
| DCP | | | | | | | | 70 | | | | | | |
| UDMA | | | | | | | | | | | | | | 70 |
| TEGDMA | | | | | | | | | 30 | 30 | 30 | | | 30 |
| Mono(meth)acrylic acid ester compound (B) | | | | | | | | | | | | | | |
| POBA | 30 | 10 | 50 | | | 30 | 30 | 30 | | | | | 30 | |
| POBMA | | | | 30 | | | | | | | | | | |
| EPPA | | | | | 30 | | | | | | | | | |
| Mono(meth)acrylic acid ester compound | | | | | | | | | | | | | | |
| MMA | | | | | | | | | | | | 30 | | |
| Mono(meth)acrylamide compound | | | | | | | | | | | | | | |
| HEAA | | | | | | | | | | | 4 | | | |
| Polymerization initiator (D) | | | | | | | | | | | | | | |
| CQ | 0.2 | 0.2 | 0.2 | 0.2 | 0.2 | 0.2 | 0.2 | 0.2 | 0.2 | | 1 | 0.2 | | |
| TPO | 0.25 | 0.25 | 0.25 | 0.25 | 0.25 | 0.25 | 0.25 | 0.25 | 0.25 | | 1.25 | 0.25 | | |
| THP | | | | | | | | | | | | | 0.5 | |
| BPO | | | | | | | | | | 2 | | | | 1.5 |
| Polymerization accelerator | | | | | | | | | | | | | | |
| JJA | 0.3 | 0.3 | 0.3 | 0.3 | 0.3 | 0.3 | 0.3 | 0.3 | 0.3 | | 1.5 | 0.3 | 1.5 | 1.5 |
| DEPT | | | | | | | | | | 2 | | | | |

Production Example 1 of Inorganic Filler

In 300 parts by mass of ethanol, 100 parts by mass of NF180 was dispersed, and 7 parts by mass of γ-MPS, 0.15 parts by mass of acetic acid, and 5 parts by mass of water were added. The resulting mixture was stirred at room temperature for 2 hours. The solvent was distilled away under reduced pressure, and furthermore was dried at 90° C. for 3 hours for surface treatment to obtain an inorganic filler (C1).

Production Example 2 of Inorganic Filler

In 300 parts by mass of ethanol, a mixture of 80 parts by mass of UF2.0 and 20 parts by mass of NF180 was dispersed, and 2.25 parts by mass of γ-MPS, 0.15 parts by mass of acetic acid, and 5 parts by mass of water were added. The resulting mixture was stirred at room temperature for 2 hours. The solvent was distilled away under reduced pressure, and furthermore was dried at 90° C. for 3 hours for surface treatment to obtain an inorganic filler (C2).

Production Example 3 of Inorganic Filler

In 300 parts by mass of ethanol, 100 parts by mass of NF180 was dispersed, and 11 parts by mass of 11-MUS, 0.15 parts by mass of acetic acid, and 5 parts by mass of water were added. The resulting mixture was stirred at room temperature for 2 hours. The solvent was distilled away under reduced pressure, and furthermore was dried at 90° C. for 3 hours for surface treatment to obtain an inorganic filler (C3).

Production Example 4 of Inorganic Filler

In 300 parts by mass of ethanol, a mixture of 90 parts by mass of UF0.7 and 10 parts by mass of Ar130 was dispersed, and 4 parts by mass of 11-MUS, 0.15 parts by mass of acetic acid, and 5 parts by mass of water were added. The resulting mixture was stirred at room temperature for 2 hours. The solvent was distilled away under reduced pressure, and furthermore was dried at 90° C. for 3 hours for surface treatment to obtain an inorganic filler (C4).

Production Example 5 of Inorganic Filler

In 300 parts by mass of toluene, a mixture of 100 parts by mass of UF1.5 and 20 parts by mass of Ox50 was dispersed, and 4 parts by mass of γ-MPS was added. The resulting mixture was heated under reflux for 2 hours. The solvent was distilled away under reduced pressure, and furthermore was dried at 90° C. for 3 hours to obtain an inorganic filler (C5) having an inorganic filler surface-treated with a surface treatment agent.

The compositions of the inorganic fillers (C1) to (C5) are shown in Table 2 below.

TABLE 2

| Component | Inorganic filler | | | | |
|---|---|---|---|---|---|
| (parts by mass) | C1 | C2 | C3 | C4 | C5 |
| Inorganic filler | | | | | |
| UF2.0 | | 80 | | | |
| UF0.7 | | | | 90 | |
| NF180 | 100 | 20 | 100 | | |
| Ar130 | | | | 10 | |
| UF1.5 | | | | | 100 |
| Ox50 | | | | | 20 |
| Surface treatment agent | | | | | |
| γ-MPS | 7 | 2.25 | | | 4 |
| 11-MUS | | | 11 | 4 | |

Production Examples 1 to 3 of Prepolymer

A mono(meth)acrylic acid ester compound, a mono(meth)acrylic acid ester compound (B), and a (meth)acrylic acid ester compound (A) were used in the amounts shown in Table 3 as polymerizable monomers. These were charged into a three-neck flask together with toluene (used in 5 times the total mass of the mono(meth)acrylic acid ester compounds and the (meth)acrylic acid ester compound). After dissolution and 30 minutes of nitrogen bubbling, a chain transfer agent and a polymerization initiator were added in the amounts shown in Table 3, and the mixture was stirred to obtain a toluene solution.

The toluene solution was stirred while being heated at 80° C. under reflux in an oil bath. After 240 minutes, the heating was stopped, the toluene solution was dropped in hexane (used in 6 times the mass of the toluene solution) to obtain a precipitate at the bottom. This was dried at ordinary temperature under reduced pressure overnight to obtain white powdery prepolymers (P1) to (P3).

The compositions of the prepolymers (P1) to (P3) are shown in Table 3 below.

TABLE 3

| | | Prepolymer | | |
|---|---|---|---|---|
| | | P1 | P2 | P3 |
| Mono(meth)acrylic acid ester compound | | | | |
| IBMA | Mole ratio | 50 | | |
| DDMA | Mole ratio | | 50 | |
| Mono(meth)acrylic acid ester compound (B) | | | | |
| EPPA | Mole ratio | | | 50 |
| (Meth)acrylic acid ester compound (A) | | | | |
| D2.6E | Mole ratio | 50 | 50 | 50 |
| Chain transfer agent | | | | |
| DPMP | Mole ratio | 60 | 60 | 60 |
| Polymerization initiator | | | | |
| BPO | Parts by mass | 2.5 | 2.5 | 2.5 |
| Weight-average molecular weight | | 47,000 | 51,000 | 41,000 |
| The number of unreacted polymerizable functional groups (average) | Number/1 mole | 29 | 33 | 37 |

[Weight-Average Molecular Weight of Prepolymer]

The weight-average molecular weight of the prepolymer was determined by GPC analysis. Specifically, tetrahydrofuran was used as an eluent, and a column was prepared by joining two "TSKgel SuperMultipore HZM-M" columns manufactured by Tosoh Corporation and one "TSKgel SuperHZ 4000" column manufactured by Tosoh Corporation, end to end. A GPC system "HLC-8320GPC" manufactured by Tosoh Corporation equipped with a differential refractive index detector (RI detector) was used as a GPC device. For measurement, 4 mg of a prepolymer was dissolved in 5 mL of tetrahydrofuran to prepare a sample solution. With the column oven temperature set to 40° C., 20 μL of the sample solution was injected at an eluent flow rate of 0.35 mL/min, and the resulting chromatogram of the prepolymer was analyzed. Separately, a standard curve relating retention time to molecular weight was created by GPC using ten polystyrene standards having a molecular weight in the 400 to 5,000,000 range. The weight-average molecular weight of the prepolymer was then determined from its chromatogram, using the standard curve (n=1).

[Number of Unreacted Polymerizable Functional Groups in Prepolymer (Average Number Per Molecule)]

The concentration ρ (mol/g) of unreacted polymerizable functional groups in a prepolymer was determined by $^1$H-NMR analysis, and multiplied by the measured weight-average molecular weight ($M_w$) ($\rho \times M_w$) to find the number of unreacted polymerizable functional groups in the prepolymer (average number per molecule).

For the $^1$H-NMR analysis, about 30 mg of weighed prepolymer and about 2 mg of weighed dimethyl terephthalate (internal standard; a molecular weight of 194.19) were dissolved in 3 mL of deuterated chloroform ($W_P$: weight of prepolymer in mg; $W_D$: weight of dimethyl terephthalate in mg). The sample was measured at room temperature by being scanned 16 times with a nuclear magnetic resonance apparatus ("ULTRA SHIELD 400 PLUS" manufactured by Bruker), and the mole ratio ($R_{P/D}$) of methacryloyl group and dimethyl terephthalate was determined from the integral values of peaks (5.55 ppm and 6.12 ppm) attributed to protons derived from the methacryloyl group, and the integral value of a peak (8.10 ppm) attributed to protons in the aromatic group of dimethyl terephthalate by the following formula.

$$R_{P/D}=[(I_{5.55}+I_{6.12})/2]/(I_{8.10}/4)$$

(where $I_{5.55}$ represents the integral value of a peak at 5.55 ppm, $I_{6.12}$ represents the integral value of a peak at 6.12 ppm, and $I_{8.10}$ represents the integral value of a peak at 8.10 ppm).

The calculated value of the mole ratio ($R_{P/D}$) of methacryloyl group and dimethyl terephthalate was then used to determine the concentration ρ [mol/g] of polymerizable functional groups in the prepolymer (n=1) by the following formula.

$$ρ=[R_{P/D}×W_D/194.19]/W_P$$

(where $W_D$ represents the weight of dimethyl terephthalate (mg) and $W_P$ represents the weight of the prepolymer (mg).)

Test Example 1 [Mechanical Strength (Three-Point Flexural Test)]

With respect to the dental composite resin, the produced dental restorative curable composition of each Example and Comparative Example was defoamed in vacuum, and then was charged into a stainless-steel mold (dimensions: 2 mm×2 mm×25 mm). With the dental restorative curable composition being pressed between glass slides from top and bottom, light was applied through the glass slides from both sides to cure the dental restorative curable composition. Here, light was applied at 5 points each side, 10 seconds at each point, using a dental LED photoirradiator for polymerization (under the trade name "PenCure 2000" manufactured by J. Morita Corp.). A total of five cured products were produced as specimens for each Example and Comparative Example. After the specimens of cured products were taken out of the mold, flexural strength and flexural modulus were measured for the specimens of cured products at a span length of 20 mm and a crosshead speed of 1 mm/min, using a precision universal testing machine (under the trade name "AG-I 100 kN" manufactured by Shimadzu Corporation). From the measured values, average values were calculated for each specimen to find the flexural strength and the flexural modulus. With respect to the dental mill blank, the measurement was performed in the same manner as the above measurement on the specimens of dental composite resin, except that, after being defoamed in vacuum, the produced dental restorative curable composition of each Example and Comparative Example was charged into a stainless-steel mold having a different size (dimensions: 1.2 mm×4 mm×14 mm), and the span length with use of the precision universal testing machine was 12 mm, and a total of 10 cured products were produced as specimens for each Example and Comparative Example. As the flexural strength of dental composite resin, 150 MPa or more is determined to be good, and 180 MPa or more is better. As the flexural modulus of dental composite resin, 8 GPa or more is determined to be good, and 10 GPa or more is better. As the flexural strength of dental mill blank, 200 MPa or more is determined to be good, and 240 MPa or more is better. As the flexural modulus of dental mill blank, 12 GPa or more is determined to be good, and 15 GPa or more is better. For the mechanical strength, those that satisfy both the criteria for the flexural strength and the flexural modulus were determined to be acceptable.

Test Example 2 [Water Resistance (Three-Point Flexural Test)]

With respect to the dental composite resin, the specimens of cured product of the produced dental restorative curable composition according to each Example and Comparative Example were immersed in water at 37° C. for 30 days, and then was measured for flexural strength and flexural modulus in the same manner as in the above Test example 1 (n=5). With respect to the dental mill blank, the measurement was performed in the same manner as in that for the dental composite resin except n=10. With use of the test result of Test example 1 as the initial flexural strength and flexural modulus, the rate of change (rate of decrease) in flexural strength and flexural modulus after immersion in water at 37° C. for 30 days was calculated by the following formula. When the rate of decrease is 10% or less, the water resistance is excellent.

Rate of decrease in flexural strength due to immersion (%)=[{initial flexural strength (MPa)−flexural strength after immersion in water (MPa)}/initial flexural strength (MPa)]×100

Rate of decrease in flexural modulus due to immersion (%)=[{initial flexural modulus (GPa)−flexural modulus after immersion in water (GPa)}/initial flexural modulus (GPa)]×100

Test Example 3 [Polishability]

The produced dental restorative curable composition of each Example and Comparative Example was defoamed in vacuum, and then was charged into a Teflon (registered trademark) mold (10 mm in inner diameter×2.0 mm in thickness). With the dental restorative curable composition being pressed between glass slides from top and bottom, light was applied through the glass slides from only above for 10 seconds using a dental LED photoirradiator for polymerization (under the trade name "PenCure 2000" manufactured by J. Morita Corp.) to cure the dental restorative curable composition to obtain a specimen (n=2). The specimen was taken out of the Teflon (registered trademark) mold, and its clean and smooth surface was polished with #600 abrasive paper under dry conditions. With use of Volvere RX (manufactured by NAKANISHI INC.) as a processing engine, the smooth surface was further polished with Brown Silicone Points (manufactured by SHOFU INC.) under flowing water conditions at a rotation speed of about 5,000 rpm for 10 seconds, following which the surface was polished with Blue Silicone Points (manufactured by SHOFU INC.) at a rotation speed about 5,000 rpm for 10 seconds. The gloss of the polished surface thus obtained was measured with a gloss meter (VG7000 manufactured by Nippon Denshoku Industries Co., Ltd.) to determine the percentage relative to 100% gloss of a mirror. The measurement angle was 60°. Average values of the measured values are shown in Tables 4 and 5. The gloss is preferably 80% or more, and more preferably 85% or more.

Test Example 4 [Paste Handling Properties (Adhesion)]

The produced dental restorative curable composition of each Example and Comparative Example was defoamed in vacuum, and then was charged into a syringe. The paste was left to stand at 25° C. for 24 hours to prepare a specimen for adhesion testing. The paste in the syringe was extruded into a cup having a volumetric dimensions measuring 11 mm in bottom face diameter, 13 mm in top face diameter, and 8 mm in height. A jig having an end with a stainless-steel cylinder measuring 10 mm in diameter×5 mm was attached to a compact table-top tester (EZ Test manufactured by Shimadzu Corporation). The bottom surface of the stainless-steel cylinder on the cylindrical jig was gently brought into contact with the paste, and then the maximum stress of when the jig was lifted at a crosshead speed of 50 mm/min was measured as adhesion to a stainless steel plate at 25° C. (n=2). Average values of the measured values are shown in Table 4. As an evaluation of the paste handling properties, the adhesion force is preferably 1.5 N or less, and more preferably 1.0 N or less. Meanwhile, an adhesion force of 2.0N or more is determined to be low in paste handling properties at filling by a dental instrument.

Test Example 5 [Polymerization Shrinkage Stress]

The dental restorative curable composition obtained in each Example or Comparative Example was charged into a ring-shaped mold (stainless steel, 5.5 mm in inner diameter× 0.8 mm in thickness) placed on a 4.0 mm-thick glass plate. The glass plate was used after being sandblasted with alumina powder having a particle diameter of 50 μm. A stainless-steel jig (5 mm in diameter), coupled to a universal testing machine (under the trade name "Autograph AG-I 100 kN" manufactured by Shimadzu Corporation), was then placed on the paste, which was charged, to sandwich the dental restorative curable composition therebetween. The paste was then cured by applying light for 20 seconds through the glass plate, using a dental LED photoirradiator for polymerization (under the trade name "PenCure 2000" manufactured by J. Morita Corp.). The polymerization shrinkage stress due to curing by the polymerization reaction of the dental restorative curable composition initiated by photoirradiation was measured with the universal testing machine (n=3). Average values of the measured values are shown in Table 4. The polymerization shrinkage stress is preferably 10.0 MPa or less, more preferably 9.8 MPa or less, even more preferably 9.5 MPa or less, and particularly preferably 9.0 MPa or less.

Test Example 6 [Air Bubble Generation Rate in Cured Product]

The produced cured product of the dental restorative curable composition according to each Example and Comparative Example was evaluated for the presence or absence of air bubbles in the interior and appearance of the cured product by using a desktop microfocus X-ray CT system (inspeXio SMX-90CT manufactured by Shimadzu Corporation) (n=10). As an evaluation of the air bubble generation rate in the cured product, the number of cured products with air bubbles is preferably 1 or less, and most preferably 0. Meanwhile, when the number of cured products with air bubbles is 3 or more, it is determined that the quality is inferior in view of decrease in mechanical strength, deterioration in appearance, and the like.

Examples 1 to 16 and Comparative Examples 1 to 4 (Dental Composite Resin)

The polymerizable monomer-containing compositions (M1) to (M12), the inorganic fillers (C1) to (C4), the inorganic fillers (C6) and (C7), and the prepolymers (P1) to (P3) obtained in the production examples were used to be kneaded at the composition ratios shown in Table 4 below for uniformization, and then were defoamed in vacuum to prepare pasty dental restorative curable compositions of Examples 1 to 16 and Comparative Examples 1 to 4. The characteristic evaluation tests (Test examples 1 to 5) were performed on the prepared dental restorative curable compositions. The results are shown in Table 4 below.

TABLE 4

| | | Example | | | | | | | | | |
|---|---|---|---|---|---|---|---|---|---|---|---|
| | | 1 | 2 | 3 | 4 | 5 | 6 | 7 | 8 | 9 | 10 |
| Inorganic filler | | | | | | | | | | | |
| | Type | (C1) | (C1) | (C1) | (C1) | (C1) | (C1) | (C1) | (C1) | (C2) | (C3) |
| | Parts by mass | 75 | 75 | 75 | 75 | 75 | 75 | 75 | 75 | 82 | 78 |
| Polymerizable monomer-containing composition | | | | | | | | | | | |
| | Type | (M1) | (M2) | (M3) | (M4) | (M5) | (M6) | (M7) | (M8) | (M1) | (M1) |
| | Parts by mass | 25 | 25 | 25 | 25 | 25 | 25 | 25 | 25 | 18 | 22 |
| Prepolymer | | | | | | | | | | | |
| | Type | | | | | | | | | | |
| | Parts by mass | | | | | | | | | | |
| Various tests | | | | | | | | | | | |
| Flexural strength (initial) | MPa | 156 | 152 | 150 | 159 | 152 | 167 | 159 | 152 | 212 | 187 |
| Flexural modulus (initial) | GPa | 10.2 | 10.8 | 9.9 | 10.4 | 10.1 | 10.8 | 10.9 | 10.5 | 14.5 | 11.3 |

TABLE 4-continued

| | | | | | | | | | | | |
|---|---|---|---|---|---|---|---|---|---|---|---|
| Flexural strength (after water immersion at 37° C. for 30 days) | MPa | 150 | 147 | 144 | 155 | 148 | 160 | 145 | 141 | 208 | 185 |
| Flexural modulus (after water immersion at 37° C. for 30 days) | GPa | 9.9 | 10.5 | 9.6 | 10.1 | 9.9 | 10.4 | 10.0 | 9.6 | 14.3 | 11.2 |
| Rate of decrease in flexural strength due to immersion | % | 3.8 | 3.3 | 4.0 | 2.5 | 2.6 | 4.2 | 8.8 | 7.2 | 1.9 | 1.1 |
| Rate of decrease in flexural modulus due to immersion | % | 2.9 | 2.8 | 3.0 | 2.9 | 2.0 | 3.7 | 8.3 | 8.6 | 1.4 | 0.9 |
| Polishability | % | 92 | 90 | 93 | 92 | 92 | 90 | 89 | 90 | 85 | 94 |
| Paste handling properties (adhesion) | N | 1.0 | 1.2 | 1.0 | 1.0 | 1.1 | 1.2 | 1.5 | 1.1 | 0.8 | 0.9 |
| Polymerization shrinkage stress | MPa | 10.4 | 10.5 | 10.3 | 10.7 | 10.0 | 10.2 | 10.5 | 10.3 | 11.6 | 10.9 |

| | | Example | | | | | | Comparative Example | | | |
|---|---|---|---|---|---|---|---|---|---|---|---|
| | | 11 | 12 | 13 | 14 | 15 | 16 | 1 | 2 | 3 | 4 |
| Inorganic filler | | | | | | | | | | | |
| Type | | (C4) | (C1) | (C1) | (C1) | (C1) | (C1) | (C1) | (C6) + (C7) | (C1) | (C1) |
| Parts by mass | | 80 | 75 | 75 | 75 | 75 | 75 | 75 | 200 + 120 | 100 | 75 |
| Polymerizable monomer-containing composition | | | | | | | | | | | |
| Type | | (M1) | (M4) | (M4) | (M4) | (M4) | (M4) | (M9) | (M10) | (M11) | (M12) |
| Parts by mass | | 20 | 18 | 20 | 22 | 20 | 20 | 25 | 100 | 320 | 25 |
| Prepolymer | | | | | | | | | | | |
| Type | | | (P1) | (P1) | (P1) | (P2) | (P3) | | | | |
| Parts by mass | | | 7 | 5 | 3 | 5 | 5 | | | | |
| Various tests | | | | | | | | | | | |
| Flexural strength (initial) | MPa | 215 | 151 | 151 | 155 | 150 | 152 | 122 | 134 | 100 | 87 |
| Flexural modulus (initial) | GPa | 13.8 | 8.6 | 9 | 9.4 | 9.1 | 9 | 9.1 | 9.5 | 8.4 | 8.8 |
| Flexural strength (after water immersion at 37° C. for 30 days) | MPa | 214 | 145 | 143 | 147 | 141 | 144 | 97 | 111 | 76 | 65 |
| Flexural modulus (after water immersion at 37° C. for 30 days) | GPa | 13.8 | 8.2 | 8.7 | 9 | 8.7 | 8.5 | 7.5 | 8.2 | 6.7 | 7.2 |
| Rate of decrease in flexural strength due to immersion | % | 0.5 | 4.0 | 5.3 | 5.2 | 6.0 | 5.3 | 20.5 | 17.2 | 24.0 | 25.3 |
| Rate of decrease in flexural modulus due to immersion | % | 0.0 | 4.7 | 3.3 | 4.3 | 4.4 | 5.6 | 17.6 | 13.7 | 20.2 | 18.2 |
| Polishability | % | 90 | 89 | 91 | 91 | 92 | 91 | 83 | 73 | 82 | 69 |
| Paste handling properties (adhesion) | N | 0.9 | 1.5 | 1.3 | 1.2 | 1.4 | 1.3 | 2.1 | 2.8 | 2.0 | 2.1 |
| Polymerization shrinkage stress | MPa | 11.2 | 8.2 | 8.7 | 9.4 | 8.9 | 8.7 | 9.9 | 10.3 | 9.5 | 9.9 |

As shown in Table 4, all of the pastes obtained in Examples 1 to 16 were good in handling properties. It was also found that their cured products had a high mechanical strength and was excellent in water resistance with no strength decrease caused by immersion in water at 37° C. assuming the oral cavity. It was further found that the cured product was excellent in polishability. In addition, in the pastes obtained in Examples 12 to 16, the polymerization shrinkage stress was reduced. In contrast, the paste obtained in Comparative Example 1 was low in mechanical strength and water resistance. Also, the paste obtained in Comparative Example 2 was slightly low in mechanical strength and water resistance, but was extremely inferior in polishability and handling properties. The pastes obtained in Comparative Examples 3 and 4 was extremely inferior in mechanical strength and water resistance, and the pastes obtained in Comparative Examples 3 and 4 was extremely inferior in polishability.

Examples 17 to 20 and Comparative Example 5
(Dental Mill Blank)

The polymerizable monomer-containing compositions (M13) and (M14) and the inorganic fillers (C1) to (C5) obtained in the production examples were used to be kneaded at the composition ratios shown in Table 5 below for uniformization, and then were defoamed in vacuum to prepare pasty dental restorative curable compositions of Examples 17 to 20 and Comparative Example 5. Next, the dental restorative curable compositions were each poured into a rectangular mold of 20 mm×30 mm×60 mm and heated at 50° C. for 1 hour. Then, a heat treatment was performed under pressure of 5 MPa at 150° C. for 1 hour to obtain a cured product as a dental mill blank. The characteristic evaluation tests (Test examples 1 to 3 and 6) were performed on the obtained cured products. The results are shown in Table 5 below.

Comparative Example 6

(1) 200 g of the inorganic filler (C5) obtained in the production example was laid on a lower punching rod of a press mold having a circular hole of 200 mm in diameter. The powder was leveled by tapping, and an upper punching rod was set above, and uniaxial pressing (press pressure: 300 kN (26.5 MPa), press time: 5 minutes) was performed using a desktop pressing machine. The upper punching rod and the lower punching rod were detached from the mold, and the resulting molded body as an aggregate of the inorganic filler (C5) was taken out. The molded body was pressed (pressure: 350 MPa, compression time: 20 minutes) by CIP to obtain an inorganic filler molded body.

(2) The obtained inorganic filler molded body was immersed in the polymerizable monomer-containing composition (M14). After removing air by decompression (10 hPa), the whole was left to stand at 70° C. for 48 hours to obtain an inorganic filler molded body impregnated with the polymerizable monomer-containing composition (polymerizable monomer impregnated molded body). The polymerizable monomer impregnated molded body was taken out, placed on a glass slide, irradiated with light for photopolymerization for 60 minutes with a UV light generator (black light fluorescent lamp manufactured by Toshiba Corporation). Then, the polymerizable monomer impregnated molded body was heated at 70° C. for 24 hours, and then at 110° C. for 5 hours with a hot-air dryer to obtain a cured product as a dental mill blank. The characteristic evaluation tests (Test examples 1 to 3 and 6) were performed on the obtained cured products. The results are shown in Table 5 below.

TABLE 5

|  |  | Example |  |  |  | Comparative Example |  |
|---|---|---|---|---|---|---|---|
|  |  | 17 | 18 | 19 | 20 | 5 | 6 |
| Inorganic filler |  |  |  |  |  |  |  |
| Type |  | (C1) | (C2) | (C3) | (C4) | (C1) | (C5) |
| Parts by mass |  | 75 | 84 | 78 | 82 | 71 | 90 |
| Polymerizable monomer-containing composition |  |  |  |  |  |  |  |
| Type |  | (M13) | (M13) | (M13) | (M13) | (M14) | (M14) |
| Parts by mass |  | 25 | 16 | 22 | 18 | 29 | 10 |
| Various tests |  |  |  |  |  |  |  |
| Flexural strength (initial) | MPa | 273 | 324 | 288 | 304 | 198 | 224 |
| Flexural modulus (initial) | GPa | 13.2 | 18.6 | 14.1 | 17.1 | 12.2 | 19.1 |
| Flexural strength (after water immersion at 37° C. for 30 days) | MPa | 266 | 313 | 283 | 297 | 171 | 183 |
| Flexural modulus (after water immersion at 37° C. for 30 days) | GPa | 12.8 | 18.2 | 13.8 | 16.8 | 10.8 | 16.3 |
| Rate of decrease in flexural strength due to immersion | % | 2.6 | 3.4 | 1.7 | 2.3 | 13.6 | 18.3 |
| Rate of decrease in flexural modulus due to immersion | % | 3.0 | 2.2 | 2.1 | 1.8 | 11.5 | 14.7 |
| Polishability | % | 93 | 86 | 93 | 91 | 82 | 78 |
| Air bubble generation rate in cured product | Piece | 0 | 0 | 0 | 0 | 5 | 3*[1] |

*[1]The number of cracks generated in fabricating polymerizable monomer impregnated molded body All of the cured products obtained in Examples 17 to 20 were free of air bubbles. It was also found that their cured products had a high mechanical strength and was excellent in water resistance with no strength decrease caused by immersion in water at 37° C. assuming the oral cavity. It was further found that the cured products were excellent in polishability. Compared with this, the cured product obtained in Comparative Example 5 had a large number of air bubbles, and was low in mechanical strength and water resistance. The cured product obtained in Comparative Example 6 was also low in water resistance, and furthermore was low in polishability.

From the above results, it was found that the dental restorative curable composition of the present invention has a high mechanical strength and excellent water resistance and polishability in the form of a cured product. It was also found that the dental restorative curable composition of the present invention is excellent in paste handling properties and can suppress air bubble generation in the cured product.

INDUSTRIAL APPLICABILITY

A dental restorative curable composition of the present invention has a high mechanical strength and excellent water resistance and polishability in the form of a cured product. Also, the dental restorative curable composition of the present invention is excellent in paste handling properties, that is, excellent in handling, and has a sufficient mechanical strength to serve as a substitute for natural teeth, and is suitably used as a material for restoring lost parts and caries of teeth, in particular as a dental composite resin. Further, its cured product is suitably used as a dental mill blank.

The invention claimed is:
1. A dental restorative curable composition, comprising:
 a (meth)acrylic acid ester compound (A) comprising two or more (meth)acryloyloxy groups per molecule;
 a mono(meth)acrylic acid ester compound (B);
 an inorganic filler (C) having an average primary particle diameter in a range of from 0.01 to 5 μm; and
 a polymerization initiator (D),
 wherein the mono(meth)acrylic acid ester compound (B) comprises at least one selected from the group consisting of a mono(meth)acrylic acid ester compound (B-1) of formula (I)

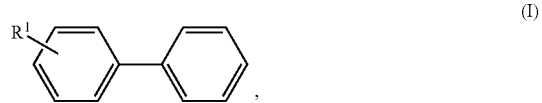

and a mono(meth)acrylic acid ester compound (B-2) represented by the following general formula (II),

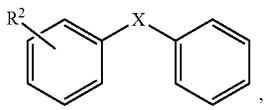

X being O or a divalent hydrocarbon group comprising 1 to 6 carbon atoms, and $R^1$ and $R^2$ each independently being a first group of formula (i)

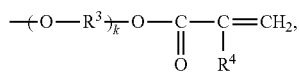

or a second group of formula (ii)

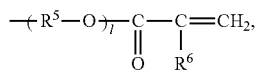

$R^3$ and $R^5$ each independently being a divalent hydrocarbon group comprising 1 to 10 carbon atoms, $R^4$ and $R^6$ each independently being H or a methyl group, and k and l each independently being an integer in a range of from 0 to 6,
wherein the inorganic filler (C) is present in a range of from 50 to 95 mass % with respect to a total mass of the dental restorative curable composition.

2. The composition of claim 1, wherein the mono(meth)acrylic acid ester compound (B) comprises the mono(meth)acrylic acid ester compound (B-2) of formula (II).

3. The composition of claim 2, wherein X is an oxygen atom.

4. The composition of claim 1, wherein k and l are each 0 or 1.

5. The composition of claim 1, wherein the (meth)acrylic acid ester compound (A) comprises a compound comprising a ring structure.

6. The composition of claim 5, wherein the compound having the ring structure is a compound (A-1) having an aromatic ring.

7. The composition of claim 6, wherein the compound (A-1) having an aromatic ring is a compound having a bisphenol A skeleton.

8. The composition of claim 1, wherein the (meth)acrylic acid ester compound (A) comprises a compound having none of a hydroxy group, a carboxy group, a primary amino group, a secondary amino group, an amide group, a urea bond, and a urethane bond.

9. The composition of claim 1, which is essentially free of a compound having a heterocyclic ring having a nitrogen atom and a polymerizable functional group.

10. The composition of claim 1, wherein the polymerization initiator (D) comprises a photopolymerization initiator.

11. The composition of claim 1, wherein the polymerization initiator (D) comprises a thermal polymerization initiator.

12. The composition of claim 1, further comprising: a polymer.

13. The composition of claim 12, wherein the polymer is a prepolymer having an unreacted polymerizable functional group.

14. The composition of claim 13, wherein a number of unreacted polymerizable functional groups per molecule in the prepolymer is in a range of from 5 to 1,000.

15. The composition of claim 13, wherein a weight-average molecular weight of the prepolymer is in a range of from 1,000 to 1,000,000.

16. A dental composite resin, comprising:
the dental restorative curable composition of claim 1.

17. A dental mill blank, comprising:
the dental restorative curable composition of claim 1.

* * * * *